US012773531B2

(12) United States Patent
Kawwas

(10) Patent No.: US 12,773,531 B2
(45) Date of Patent: Oct. 27, 2026

(54) MULTI-FUNCTION CATHETER SHAFT TOOL

(71) Applicant: Medtronic Ireland Manufacturing Unlimited Company, Dublin (IE)

(72) Inventor: Jaclyn N. Kawwas, Philadelphia, PA (US)

(73) Assignee: Medtronic Ireland Manufacturing Unlimited Company, Dublin (IE)

(*) Notice: Subject to any disclaimer, the term of this patent is extended or adjusted under 35 U.S.C. 154(b) by 372 days.

(21) Appl. No.: 18/554,047

(22) PCT Filed: Apr. 26, 2022

(86) PCT No.: PCT/EP2022/061010
§ 371 (c)(1),
(2) Date: Oct. 5, 2023

(87) PCT Pub. No.: WO2022/229160
PCT Pub. Date: Nov. 3, 2022

(65) Prior Publication Data

US 2024/0108858 A1 Apr. 4, 2024

Related U.S. Application Data

(60) Provisional application No. 63/179,895, filed on Apr. 26, 2021.

(51) Int. Cl.
*A61M 25/01* (2006.01)
*A61M 25/09* (2006.01)

(52) U.S. Cl.
CPC .... *A61M 25/0113* (2013.01); *A61M 25/0136* (2013.01); *A61M 25/09* (2013.01)

(58) Field of Classification Search
CPC .............. A61M 25/01; A61M 25/0113; A61M 25/0136; A61M 25/0194; A61M 25/09;
(Continued)

(56) References Cited

U.S. PATENT DOCUMENTS 5,054,501 A 10/1991 Chuttani et al.
9,867,982 B2 1/2018 Berthiaume et al.
(Continued)

FOREIGN PATENT DOCUMENTS

CN 103945898 A 7/2014
EP 2875842 A1 5/2015
(Continued)

OTHER PUBLICATIONS

International Preliminary Report on Patentability from International Application No. PCT/EP2022/061010 dated Oct. 24, 2023, 8 pp.
(Continued)

*Primary Examiner* — Katherine M Rodjom
(74) *Attorney, Agent, or Firm* — Shumaker & Sieffert, P.A.

(57) ABSTRACT

A multi-function catheter shaft tool is disclosed. A catheter shaft straightener of the tool may be used to straighten a distal end section of a catheter shaft when directed within the catheter shaft straightener. A catheter shaft actuator of the tool may be used to torque the catheter shaft, advance the catheter shaft relative to a patient's vasculature, or both. The catheter shaft straightener and the catheter shaft actuator are structurally connected (i.e., an integrated structure).

18 Claims, 20 Drawing Sheets

(58) Field of Classification Search
CPC .. A61M 25/09041; A61M 2025/09116; A61M 2025/09125
See application file for complete search history.

(56) References Cited

U.S. PATENT DOCUMENTS

| | | | | |
|---|---|---|---|---|
| 10,537,306 | B2 | 1/2020 | Schaer et al. | |
| 2007/0171540 | A1 | 7/2007 | Veldman et al. | |
| 2016/0113713 | A1 | 4/2016 | Ku et al. | |
| 2020/0061340 | A1 | 2/2020 | Mixter et al. | |
| 2020/0108236 | A1* | 4/2020 | Salazar | A61M 25/0662 |
| 2021/0001086 | A1 | 1/2021 | Berul et al. | |

FOREIGN PATENT DOCUMENTS

| | | | |
|---|---|---|---|
| WO | 2010107698 | A2 | 9/2010 |
| WO | 2019116102 | A2 | 6/2019 |

OTHER PUBLICATIONS

International Search Report and Written Opinion of International Application No. PCT/EP2022/061010 dated Sep. 23, 2022, 12 pp.
Office Action from U.S. Appl. No. 18/556,777 dated Feb. 25, 2026, 9 pp.
First Office Action and Search Report, and translation thereof, from counterpart Chinese Application No. 202280027135.X dated Jul. 24, 2026, 15 pp.

* cited by examiner

MULTI-FUNCTION CATHETER SHAFT TOOL

This application is a U.S. National Stage entry under 35 U.S.C. § 371 of International Application No. PCT/EP2022/061010, filed Apr. 26, 2022, which claims priority from and the benefit of U.S. Provisional Patent Application No. 63/179,895, filed Apr. 26, 2021, the entire content of each of which is incorporated herein by reference.

FIELD

The present disclosure generally relates to the field of catheters (e.g., neuromodulation; denervation) and, more particularly, to straightening a catheter shaft.

BACKGROUND

At least some catheters have a catheter shaft that incorporates a non-linear catheter shaft section at an appropriate location along the length of the catheter shaft. For instance, some diagnostic catheters have a pigtail curve along a portion of the catheter shaft. Certain neuromodulation and/or renal denervation catheters utilize a catheter shaft with a distal end section having a helical or spiral configuration. One or more electrodes may be spaced along such a distal end section. A guide wire may be directed through a lumen of at least the distal end section of the catheter shaft. Such a guide wire retains the distal end section in a delivery configuration where the catheter shaft may be directed into/through the vasculature of a patient. Once the distal end section of the catheter shaft is in the desired location within the vasculature, the guide wire may be withdrawn from the distal end section of the catheter shaft such that it expands within the vasculature, typically into contact with an inner wall of the vasculature. Standalone catheter shaft straighteners exist to facilitate insertion of the guide wire into/through the distal end section of the catheter shaft, and are generally in the form of a tube.

A handle of a neuromodulation catheter is typically used to torque the catheter shaft and to advance the catheter shaft within the patient's vasculature. Torqueing and/or advancement of the catheter shaft may be undertaken during repositioning, within the vasculature, of a deployed distal end section of a catheter shaft of the above-noted type.

Options for introducing a catheter into the patient's vasculature include using a femoral access, a radial access, a brachial access, and the like. The distance between a typical femoral access and the renal artery is typically significantly less than the distance between a typical radial access and the same renal artery. As such, the same renal neuromodulation/denervation catheter is typically sold in two different configurations for these different vasculature accesses. The catheter shaft of a renal neuromodulation/denervation catheter for a radial access is typically longer than the catheter shaft of a renal neuromodulation/denervation catheter for a femoral access.

SUMMARY

The present invention is directed to a multi-function catheter shaft tool. Both the configuration of such a multi-function catheter shaft tool and operational characteristics, operation, assembly, and manufacture of such a multi-function catheter shaft tool are within the scope of this Summary. The multi-function catheter shaft tool may be used in conjunction with a catheter of any appropriate type and that provides any appropriate function or combination of functions when disposed in a patient's vasculature (e.g., diagnostic, therapeutic, neuromodulation, denervation).

A multi-function catheter shaft tool in accordance with the present invention includes a tool distal end and a tool proximal end. The spacing between the tool distal end and the tool proximal end may define/correspond with a length dimension of the tool. In any case, a lumen extends through an entire length of the multi-function catheter shaft tool and is sized to accommodate a catheter shaft. As such, a catheter shaft can extend completely through the multi-function catheter shaft tool (e.g., the multi-function catheter shaft tool may be mounted on a catheter shaft).

The multi-function catheter shaft tool further includes both a catheter shaft straightener and a catheter shaft actuator (e.g., for actuating or moving the catheter shaft relative to the patient's vasculature in some fashion) that are collectively rotatable (e.g., about the length dimension of the tool). The catheter shaft straightener extends distally of the catheter shaft actuator (e.g., a proximal end portion of the catheter shaft straightener may extend at least into a distal end of the catheter shaft actuator), and may include the noted tool distal end. The multi-function catheter shaft tool also includes a catheter shaft clamp that is disposable in each of a clamping configuration and a released configuration.

A number of feature refinements and additional features are applicable to the present invention. These feature refinements and additional features may be used individually or in any combination. Disposing the catheter shaft clamp in the released configuration allows the multi-function catheter shaft tool to be moved along and relative to the length of the catheter shaft to a desired position, and the catheter shaft clamp may then be disposed in its clamping configuration. For instance, the multi-function catheter shaft tool may be moved in a distal direction when mounted on a catheter shaft (e.g., away from a catheter handle) such that a distal end section of the catheter shaft is directed into the catheter shaft straightener. Advancing the multi-function catheter shaft tool in a distal direction, relative to the catheter shaft, and with the distal end section of the catheter shaft being introduced into the catheter shaft straightener, may be used reduce the profile of the distal end section of the catheter shaft (e.g., to accommodate directing a guide wire into a lumen that extends from the distal end of the catheter shaft and in a proximal direction). However, the catheter shaft straightener may be used to move/force any length segment of a catheter shaft toward a "straighter" profile. For instance, a catheter shaft may include one or more curves along its length dimension, and the catheter shaft straightener may be used to reduce the curvature of one or more portions of the catheter shaft.

Disposing the catheter shaft clamp in its clamping configuration may be used for any appropriate purpose, including loading a catheter shaft onto a guide wire. A user may engage the catheter shaft actuator (or a grip or a gripping section for the multi-function catheter shaft tool), to torque the catheter shaft, to advance the catheter shaft within/along the vasculature of a patient (e.g., by pushing or pulling on the catheter shaft actuator), or both, all with the catheter shaft clamp being disposed in its clamping configuration. With the catheter shaft being in its released configuration, the multi-function catheter shaft tool may be advanced along and relative to the catheter shaft in the direction of a patient vasculature access to dispose the catheter shaft actuator in a desired spaced relation to this patient vasculature access, at which time the catheter shaft clamp may be disposed in the clamping configuration for use of the multi-function catheter shaft tool in accordance with the foregoing.

The lumen may be of any appropriate size and/or shape, and includes any passageway or "open space" that accommodates a catheter shaft extending completely through the multi-function catheter shaft tool, proceeding from the tool distal end to the tool proximal end. All or a portion of the lumen that extends along an entire length of the catheter shaft straightener may be defined by an annular inner wall. At least a portion of the catheter shaft straightener that interfaces with a catheter shaft, when the multi-function tool is mounted on the catheter shaft, may be formed from a material that is "softer" than portions of the multi-function tool that do not interface with the catheter shaft. For instance, interfacing portions of the catheter shaft straightener (that interface with the catheter shaft) may be formed from materials such as silicone or the like.

The catheter shaft actuator may be incorporated at any appropriate portion along the length of the multi-function catheter shaft tool, including at a proximal end of the tool. However, at least part of the catheter shaft straightener should extend distally of a distal end of the catheter shaft actuator. One embodiment has an effective outer diameter of the catheter shaft actuator being greater than an effective outer diameter of the catheter shaft straightener. The catheter shaft actuator may also be characterized as a grip or the like (e.g., to accommodate engagement by a user when actuating/moving the catheter shaft in accordance with the foregoing).

The multi-function catheter shaft tool may further include a clamping actuator that is operatively interconnected with the catheter shaft clamp. The clamping actuator may be of any appropriate configuration, but is movable between at least two different positions to accommodate changing the catheter shaft clamp between its clamping configuration and its released configuration. One embodiment has the catheter shaft actuator being in the form of a cap that is detachably engaged (e.g., via a threaded connection) with the catheter shaft straightener. Advancing the catheter shaft actuator, relative to the catheter shaft straightener and in the direction of the tool distal end, may be utilized to change the catheter shaft clamp from its released configuration to its clamping configuration. In this instance the catheter shaft actuator also functions as the clamping actuator. Advancing the catheter shaft actuator, relative to the catheter shaft straightener and away from the tool distal end, may be utilized to change the catheter shaft clamp from its clamping configuration to its released configuration. The clamping actuator could also be configured for movement relative to the catheter shaft actuator, and may be disposed at any appropriate location of the multi-function catheter shaft tool (e.g., disposed on an exterior of the catheter shaft actuator).

Further disclosed herein is a multi-function catheter shaft tool, wherein a catheter shaft straightener of the tool may be used to straighten a distal end section of a catheter shaft when directed within the catheter shaft straightener, wherein a catheter shaft actuator of the tool may be used to torque the catheter shaft, advance the catheter shaft relative to a patient's vasculature, or both, and wherein the catheter shaft straightener and the catheter shaft actuator are structurally connected (i.e., an integrated structure).

Various aspects of the present disclosure are also addressed by the following paragraphs and in the noted combinations:

1. A multi-function catheter shaft tool, comprising:
   - a tool distal end;
   - a tool proximal end;
   - a lumen that extends from said tool distal end to said tool proximal end, wherein said lumen is sized to accommodate a catheter shaft;
   - a catheter shaft straightener comprising said tool distal end;
   - a catheter shaft actuator, wherein said catheter shaft straightener extends proximally from said tool distal end and at least to a distal end of said catheter shaft actuator, wherein said catheter shaft straightener and said catheter shaft actuator are configured to be collectively rotatable; and
   - a catheter shaft clamp disposable in each of a clamping configuration and a released configuration relative to said lumen.
2. The multi-function catheter shaft tool of paragraph 1, wherein said catheter shaft straightener comprises a flared distal end section, which in turn comprises said tool distal end.
3. The multi-function catheter shaft tool of any of paragraphs 1-2, wherein said catheter shaft straightener comprises silicone.
4. The multi-function catheter shaft tool of any of paragraphs 1-3, further comprising a clamping actuator operatively interconnected with said catheter shaft clamp.
5. The multi-function catheter shaft tool of paragraph 4, wherein an exterior of said catheter shaft actuator comprises said clamping actuator.
6. The multi-function catheter shaft tool of paragraph 1, wherein said catheter shaft straightener comprises:
   - a liner, wherein said lumen extends through said liner; and
   - an outer housing disposed about said liner along at least part of a length of said liner.
7. The multi-function catheter shaft tool of paragraph 6, wherein said liner comprises a flared distal end section, which in turn comprises said tool distal end.
8. The multi-function catheter shaft tool of any of paragraphs 6-7, wherein said liner comprises a first hardness and said outer housing comprises a second hardness that is greater than said first hardness.
9. The multi-function catheter shaft tool of any of paragraphs 6-8, wherein said outer housing is more rigid than said liner.
10. The multi-function catheter shaft tool of any of paragraphs 6-9, wherein said liner extends distally beyond a distal end of said outer housing, and wherein said liner comprises said tool distal end.
11. The multi-function catheter shaft tool of any of paragraphs 6-10, wherein said catheter shaft clamp comprises a clamping section that is interconnected with a proximal end of said liner, wherein said clamping section extends proximally of said outer housing.
12. The multi-function catheter shaft tool of paragraph 11, wherein said clamping section is of a hardness that is greater than a hardness of said liner.
13. The multi-function catheter shaft tool of any of paragraphs 11-12, wherein said clamping section is formed from a first material, said liner is formed from a second material, and said first and second materials are different from one another.
14. The multi-function catheter shaft tool of any of paragraphs 11-13, wherein said clamping section comprises at least two inwardly deflectable sections.
15. The multi-function catheter shaft tool of paragraph 14, wherein an interior of said catheter shaft actuator engages both said outer housing and said at least two inwardly deflectable sections of said clamping section.

16. The multi-function catheter shaft tool of any of paragraphs 14-15, wherein advancement of said catheter shaft actuator toward said tool distal end and relative to said catheter shaft straightener moves said deflectable sections of said clamping section in a radially inward direction.

17. The multi-function catheter shaft tool of any of paragraphs 14-15, wherein said catheter shaft actuator is detachably engageable with said outer housing.

18. The multi-function catheter shaft tool of paragraph 17, wherein a proximal end section of said outer housing comprises external threads and said catheter shaft actuator comprises internal threads that threadably engage with said external threads of said proximal end section of said outer housing.

19. The multi-function catheter shaft tool of paragraph 18, wherein threading said catheter shaft actuator toward said tool distal end exerts a radially inwardly directed force on said at least two inwardly deflectable sections of said clamping section.

20. The multi-function catheter shaft tool of any of paragraphs 6-13, wherein said catheter shaft actuator is detachably engageable with said outer housing.

21. The multi-function catheter shaft tool of paragraph 20, wherein a proximal end section of said outer housing comprises external threads and said catheter shaft actuator comprises internal threads that threadably engage with said external threads of said proximal end section of said outer housing.

22. The multi-function catheter shaft tool of paragraph 21, wherein threading said catheter shaft actuator toward said tool distal end changes said catheter shaft clamp from said released configuration to said clamping configuration.

23. The multi-function catheter shaft tool of paragraph 22, wherein threading said catheter shaft actuator away from said tool distal end changes said catheter shaft clamp from said clamping configuration to said released configuration.

24. The multi-function catheter shaft tool of any of paragraphs 6-23, wherein said liner comprises silicone.

25. The multi-function catheter shaft tool of any of paragraphs 1-24, wherein an outer diameter of said catheter shaft actuator is greater than a maximum outer diameter of said catheter shaft straightener.

26. The multi-function catheter shaft tool of any of paragraphs 1-25, wherein said catheter shaft actuator is operable to at least one of torque a catheter shaft and advance a catheter shaft when extending through said lumen and when said catheter shaft clamp is disposed in said clamping configuration.

27. A catheter system comprising the multi-function catheter shaft tool of any of paragraphs 1-26 and a catheter, wherein said catheter comprises a catheter shaft that in turn comprises a first non-linear section, wherein said first non-linear section of said catheter shaft is forced into a straighter profile when disposed within said catheter shaft straightener compared to when said first non-linear section of said catheter shaft is disposed distally beyond said catheter shaft straightener.

28. The catheter system of paragraph 27, wherein said first non-linear section of said catheter shaft defines a distal end section of said catheter shaft.

29. The catheter system of any of paragraphs 27-28, wherein said catheter comprises a catheter handle, and wherein said catheter shaft actuator is disposed distally of said catheter handle.

30. A method of manipulating a catheter, said catheter comprising a catheter shaft that in turn comprises a first non-linear section, said method comprising:
- directing said first non-linear section of said catheter shaft into a distal end of a multi-function catheter shaft tool to dispose said first non-linear section of said catheter shaft within a catheter shaft straightener of said multi-function catheter shaft tool;
- forcing said first non-linear section of said catheter shaft toward a straighter profile from said directing step;
- executing a first moving step comprising moving said multi-function catheter shaft tool in a proximal direction along and relative to said catheter shaft, some time after said forcing step, and with said multi-function catheter shaft tool being in a released configuration;
- disposing said multi-function catheter shaft tool in a clamping configuration where said multi-function catheter shaft tool engages an exterior of said catheter shaft and that is executed some time after said first moving step; and
- moving said catheter shaft with said multi-function catheter shaft tool being in said clamping configuration and by exerting an external force on said multi-function catheter shaft tool.

31. The method of paragraph 30, wherein said first non-linear section comprises a distal end section of said catheter shaft.

32. The method of any of paragraphs 30-31, wherein said first non-linear section of said catheter shaft is in an expanded configuration without any force being exerted on said first non-linear section of said catheter shaft, and wherein said forcing step comprises reducing a profile step of said first non-linear section of said catheter shaft.

33. The method of any of paragraphs 30-32 wherein said multi-function catheter shaft tool is mounted on said catheter shaft with said multi-function catheter shaft tool being located proximally of said first non-linear section of said catheter shaft, and wherein said directing step comprises distally advancing said multi-function catheter shaft tool along said catheter shaft in a direction of said first non-linear section of said catheter shaft.

34. The method of any of paragraphs 30-33, wherein said first moving step comprises moving said multi-function catheter shaft tool in a direction of a handle of said catheter.

35. The method of any of paragraphs 30-34, wherein said disposing said multi-function catheter shaft tool in a clamping configuration step comprises exerting a clamping force on said exterior of said catheter shaft.

36. The method of any of paragraphs 30-35, wherein said disposing said multi-function catheter shaft tool in a clamping configuration step comprises rotating an actuator of said multi-function catheter shaft tool relative to said catheter shaft straightener.

37. The method of any of paragraphs 30-35, wherein said disposing said multi-function catheter shaft tool in a clamping configuration step comprises moving a clamping actuator from a first position to a second position to change said multi-function catheter shaft tool from said released configuration to said clamping configuration.

38. The method of any of paragraphs 30-37, wherein said moving said catheter shaft step comprises engaging a grip of said multi-function catheter shaft tool.

39. The method of any of paragraphs 30-38, wherein said moving said catheter shaft step is executed when said catheter shaft is disposed within a vasculature of a patient and with said multi-function catheter shaft tool being disposed outside of a body of said patient.

40. The method of any of paragraphs 30-39, wherein said moving said catheter shaft step comprises torqueing said catheter shaft.

41. The method of any of paragraphs 30-40, wherein said moving said catheter shaft step comprises moving an entirety of said multi-function catheter shaft tool, including said catheter shaft straightener, in a rotational direction.

42, The method of any of paragraphs 30-41, wherein said moving said catheter shaft step further comprises advancing said catheter shaft along a vasculature of a patient.

43. The method of any of paragraphs 30-42, wherein said moving said catheter shaft step comprises engaging a catheter shaft actuator of said multi-function catheter shaft tool, wherein said catheter shaft straightener extends distally from said catheter shaft actuator, 44. The method of paragraph 43, wherein an effective outer diameter of said catheter shaft actuator is greater than an effective outer diameter of said catheter shaft straightener.

45. The method of any of paragraphs 30-44, further comprising:
loading a guidewire into a distal end of said catheter shaft after said forcing step.

46, The method of paragraph 45, wherein said first moving step is executed after said loading step.

DETAILED DESCRIPTION

Figure 1A:
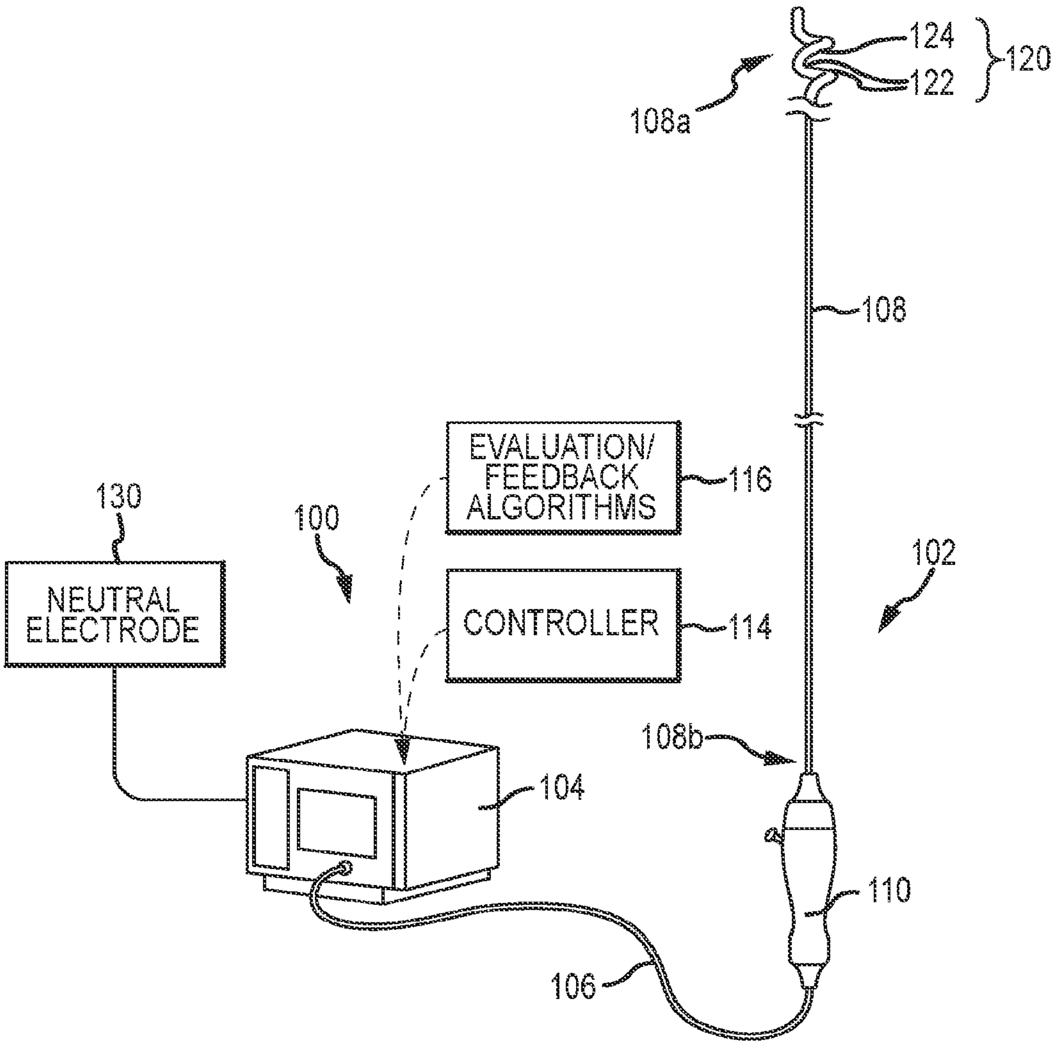
FIG.1A (PRIOR ART)
FIG. 1A is a schematic of a neuromodulation/denervation system.

The present disclosure is applicable to apparatuses and methods for achieving electrically and/or thermally-induced neuromodulation/denervation (e.g., rendering neural fibers that innervate the kidney inert, inactive or otherwise completely or partially reduced in function) by percutaneous transluminal intravascular access. Embodiments of the present technology relate to a treatment device (e.g., treatment catheter) having a therapeutic assembly (e.g., one or more energy elements) on a distal portion of the catheter shaft. After deployment in a target blood vessel of a human patient, the distal portion of the assembly is transformable between a delivery state having a low-profile that is configured to pass through the vasculature and a deployed state having a radially expanded shape (e.g., generally spiral/helical or coil) in which the distal portion is maintained in stable apposition with an inner wall of the target blood vessel (e.g., renal artery).

The system can also include an energy source or energy generator external to the patient in electrical communication with energy elements of the therapeutic assembly. In operation, the energy elements are advanced to a target blood vessel, such as the renal artery, along a percutaneous transluminal path (e.g., a femoral artery puncture, an iliac artery and the aorta, a radial artery, or another suitable intravascular path), and then energy is delivered to the wall of the target blood vessel via the energy elements. Suitable energy modalities include, for example, electrical energy, radio frequency (RF) energy, pulsed electrical energy, ultrasound, or thermal energy. The treatment device carrying the energy elements can be configured such that the energy elements are in constant apposition with the interior wall of the target blood vessel when in the deployed state (e.g., radially expanded to have a spiral/helical shape). The pre-formed spiral/helical shape of the deployed portion allows blood to flow through the assembly during therapy, which is expected to help cool the therapy assembly to prevent clot formation that may result in occlusion of the blood vessel during activation of the energy elements. The spiral/helical shape also enhances the apposition of the energy elements with the inner wall of target blood vessels and makes the therapeutic assembly adaptable to a range of vessel diameters. The largest diameter vessel in the range is at least slightly smaller than the free or un-constrained diameter of the pre-formed spiral/helical shape in order to provide and maintain adequate contact between the energy elements and the vessel wall.

Specific details of several embodiments are described herein. Although many of the embodiments are described with respect to devices, systems, and methods for intravascular renal neuromodulation, other applications and other embodiments in addition to those described herein are within the scope of the present technology. For example, at least some embodiments of the present technology may be useful for intraluminal neuromodulation, extravascular neuromodulation, non-renal neuromodulation, and/or use in therapies other than neuromodulation. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms “distal” and “proximal” define a position or direction with respect to a clinician or a clinician’s control device (e.g., a handle of a neuromodulation catheter). The terms, “distal”, “distally”, or the like refer to a position distant from or in a direction away from a clinician or a clinician’s control device along the length of device. The terms “proximal”, “proximally”, or the like refer to a position near or in a direction toward a clinician or a clinician’s control device along the length of device.

FIG. 1A is a schematic of a neuromodulation/denervation system 100. The system 100 100 includes a neuromodulation/denervation catheter 102, a console 104, and a cable 106 extending therebetween. Cable 106 may provide a permanent connection between catheter 102 and console 104, or cable 106 may be disconnectable (e.g. to permit the use of console 104 with different catheters). The neuromodulation/denervation catheter 102 can include an elongated shaft 108 having a proximal portion 108*b*, a distal portion 108*a*, a handle 110 operably connected to the shaft 108 at the proximal portion 108*b*, and a neuromodulation/denervation assembly 120 operably connected to and/or comprising at least a part of the distal portion 108*a*. The diameter of shaft 108 and the neuromodulation/denervation assembly 120 can be 2, 3, 4, 5, 6, or 7 French or another suitable size. The neuromodulation/denervation assembly 120 can include two or more metallic elements 122 that extend longitudinally along at least a portion of the length of the neuromodulation/denervation assembly 120 and a dielectric material 124 between the metallic elements 122. The metallic elements 122 can be elongated electrodes that extend longitudinally along the neuromodulation/denervation assembly 120 and are configured to apply electrical stimuli (e.g., RF energy) to target sites at or proximate to vessels within a patient, to temporarily stun nerves, to deliver neuromodulation energy to target sites, and/or to detect vessel impedance. In various embodiments, certain metallic elements 122 can be dedicated to applying stimuli and/or detecting impedance, and the neuromodulation/denervation assembly 120 can include other types of therapeutic elements that provide neuromodulation therapy using various modalities, such cryotherapeutic cooling, ultrasound energy, etc. The dielectric material 124 can be an elongated element that extends along at least a portion of the length of the neuromodulation/denervation assembly 120 and separates the metallic elements 122 from each other along at least a portion of the length of the metallic elements 122.

Figure 1B:
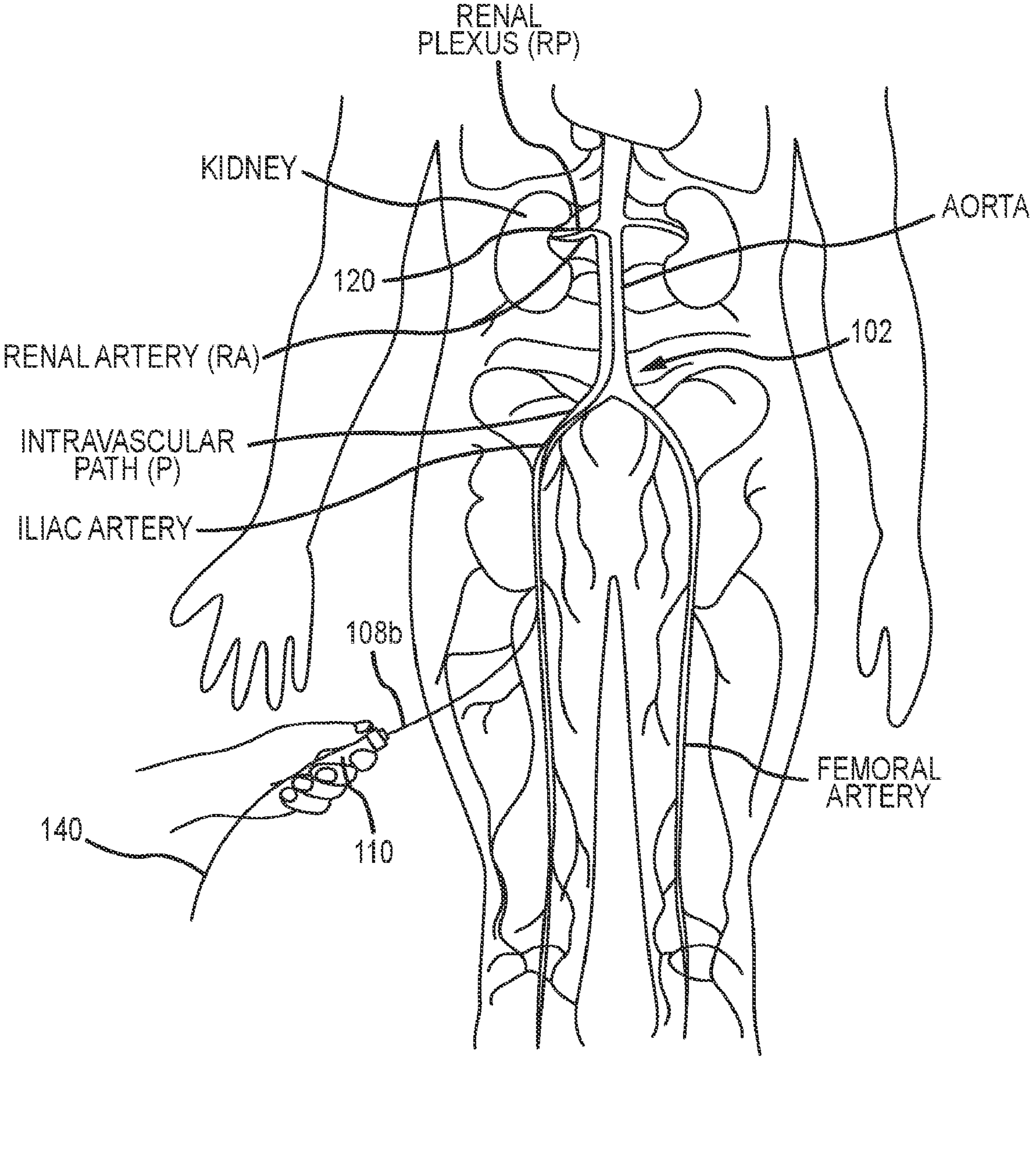
FIG. 1B is a schematic of introducing a catheter shaft of the neuromodulation/denervation system of FIG. 1A into a patient's vasculature through a femoral access.

The distal portion 108*a* of the shaft 108 is configured to be moved within a lumen of a human patient and locate the neuromodulation/denervation assembly 120 at a target site within or otherwise proximate to the lumen. For example, shaft 108 can be configured to position the neuromodulation/denervation assembly 120 within a blood vessel, a duct, an airway, or another naturally occurring lumen within the human body. In certain embodiments, intravascular delivery of the neuromodulation/denervation assembly 120 includes percutaneously inserting a guide wire 140 (FIG. 1B) into a body lumen of a patient and moving the shaft 108 and/or the neuromodulation/denervation assembly 120 along the guide wire until the neuromodulation/denervation assembly 120 reaches a target site (e.g., a renal artery). For example, the distal end of the neuromodulation/denervation assembly 120 or other part of the distal portion 108*a* of the shaft 108 may include a passageway for engaging (e.g., receiving) the guide wire for delivery of the neuromodulation/denervation assembly 120 using over-the-wire (OTW) or rapid exchange (RX) techniques. In other embodiments, the neuromodulation/denervation catheter 102 can be a steerable or non-steerable device configured for use without a guide wire. In still other embodiments, the neuromodulation/denervation catheter 102 can be configured for delivery via a guide catheter or sheath.

Once at the target site, the neuromodulation/denervation assembly 120 can be configured to apply stimuli, detect resultant hemodynamic responses, and provide or facilitate neuromodulation therapy at the target site (e.g., using the metallic elements 122 and/or other energy delivery elements). For example, the neuromodulation/denervation assembly 120 can detect vessel impedance via the metallic elements 122, detect blood flow via a flow sensing element (e.g., a Doppler velocity sensing element (not shown)), detect local blood pressure within the vessel via a pressure transducer or other pressure sensing element (not shown), and/or detect other hemodynamic parameters. The detected hemodynamic responses can be transmitted to the console 104 and/or another device external to the patient. The console 104 can be configured to receive and store the recorded hemodynamic responses for further use by a clinician or operator. For example, a clinician can use the hemodynamic responses received by the console 104 to determine whether an application of neuromodulation energy was effective in modulating nerves to a desired degree.

The console 104 can be configured to control, monitor, supply, and/or otherwise support operation of the neuromodulation/denervation catheter 102. The console 104 can further be configured to generate a selected form and/or magnitude of energy for delivery to tissue at the target site via the neuromodulation/denervation assembly 120, and therefore the console 104 may have different configurations depending on the treatment modality of the neuromodulation/denervation catheter 102. For example, when the neuromodulation/denervation catheter 102 is configured for electrode-based, heat-element-based, or transducer-based treatment, the console 104 can include an energy generator (not shown) configured to generate RF energy (e.g., monopolar and/or bipolar RF energy), pulsed electrical energy, microwave energy, optical energy, ultrasound energy (e.g., intravascularly delivered ultrasound, and/or HIFU), direct heat energy, radiation (e.g., infrared, visible, and/or gamma radiation), and/or another suitable type of energy. When the neuromodulation/denervation catheter 102 is configured for cryotherapeutic treatment, the console 104 can include a refrigerant reservoir (not shown), and can be configured to supply the neuromodulation/denervation catheter 102 with refrigerant. Similarly, when the neuromodulation/denervation catheter 102 is configured for chemical-based treatment (e.g., drug infusion), the console 104 can include a chemical reservoir (not shown) and can be configured to supply the neuromodulation/denervation catheter 102 with one or more chemicals. In some embodiments, the console 104 can include one or more fluid reservoirs (not shown) for coolant and/or irrigant (e.g., saline) to be delivered to the metallic elements 122 and/or the dielectric material 124.

In selected embodiments, the system 100 may be configured to deliver a monopolar electric field via one or more of the metallic elements 122. In such embodiments, a neutral or dispersive electrode 130 may be electrically connected to the console 104 and attached to the exterior of the patient. In embodiments including multiple metallic elements 122, the metallic elements 122 may deliver power independently (i.e., may be used in a monopolar fashion), either simultaneously, selectively, or sequentially, and/or may deliver power between any desired combination of the metallic elements 122 (i.e., may be used in a bipolar fashion). In addition, an operator optionally may be permitted to choose which metallic elements 122 are used for power delivery in order to form customized lesion(s) within the renal artery, as desired. One or more sensing elements (not shown), such as one or more temperature (e.g., thermocouple, thermistor, etc.), pressure, optical, flow, chemical, and/or other sensing elements, may be located proximate to, within, or integral with the metallic elements 122. The sensing element(s) and the metallic elements 122 can be connected to one or more supply wires (not shown) that transmit signals from the sensing element(s) and/or convey energy to the metallic elements 122.

In various embodiments, the system 100 can further include a controller 114 communicatively coupled to the neuromodulation/denervation catheter 102. The controller 114 can be configured to initiate, terminate, and/or adjust operation of one or more components (e.g., the metallic elements 122) of the neuromodulation/denervation catheter 102 directly and/or via the console 104. In other embodiments, the controller 114 can be omitted or have other suitable locations (e.g., within the handle 110, along the cable 106, etc.). The controller 114 can be configured to execute an automated control algorithm and/or to receive control instructions from an operator. Further, the console 104 can be configured to provide feedback to an operator before, during, and/or after a treatment procedure via an evaluation/feedback algorithm 116.

Figure 2:
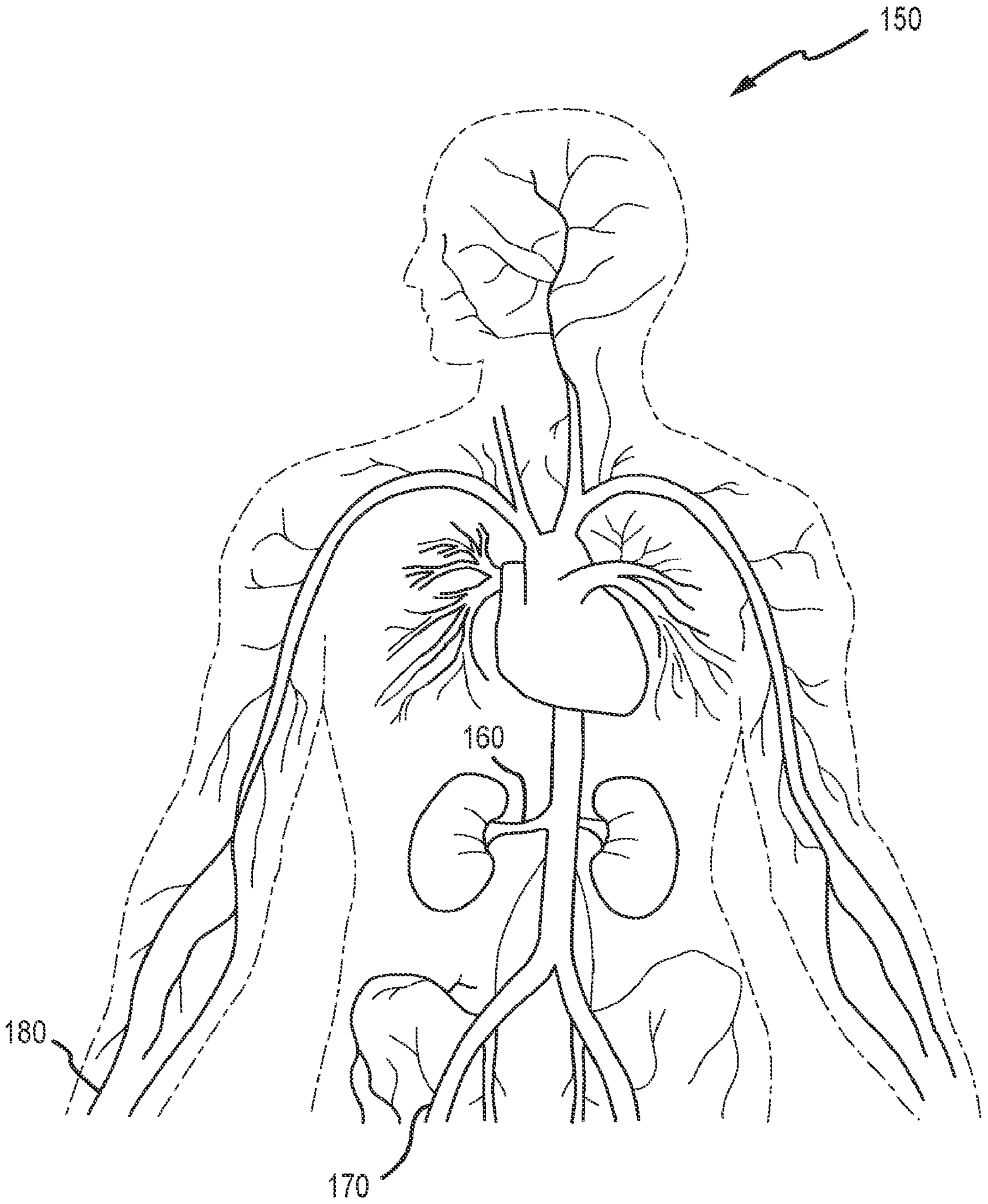
FIG. 2 is a schematic of a vasculature of a patient, illustrating both a typical femoral access and a radial access.

A schematic of a vasculature for a patient 150 is presented in FIG. 2. The renal artery 160, a representative femoral access 170, and a representative radial access 180 are shown in relation to this vasculature. A catheter (e.g., catheter 220*a* shown in FIG. 4A and addressed below) may be introduced through the femoral access 170 and may be directed through the patient's vasculature to reach a renal artery 160. A catheter (e.g., catheter 220*b* shown in FIG. 4B and addressed below) may also be introduced through the radial access 180 and may be directed through the patient's vasculature to reach a renal artery 160.

Figure 3A:
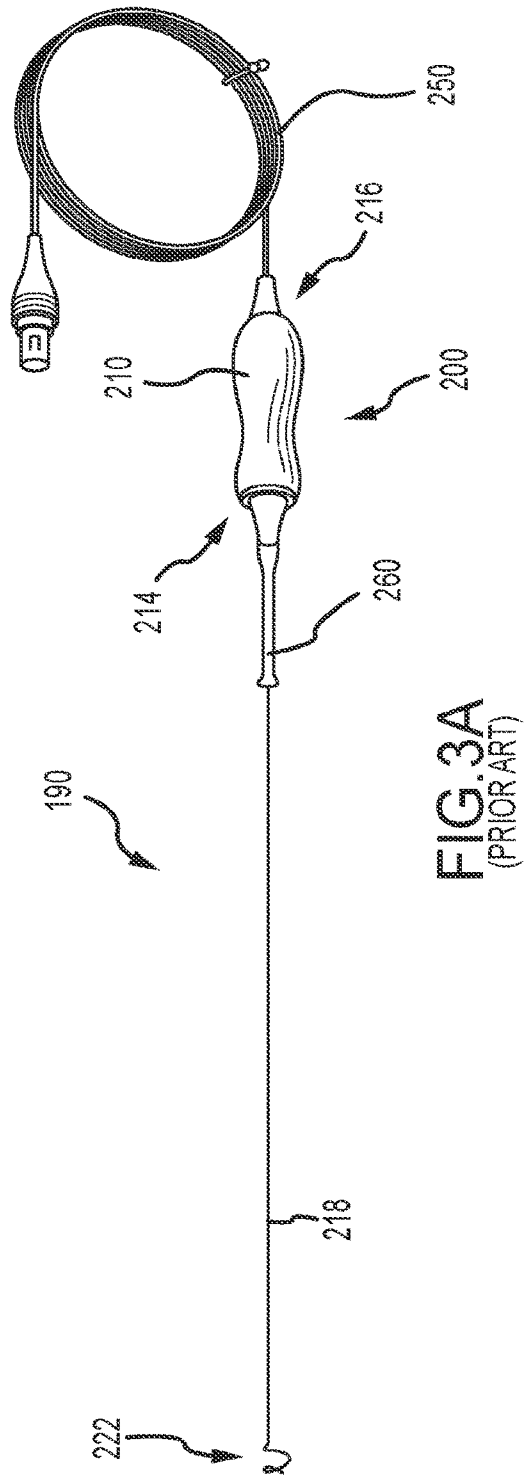
FIG.3A (PRIOR ART)
FIG. 3A is a perspective view of a prior art neuromodulation/denervation catheter with a standalone catheter shaft straightener.
Figure 3B:
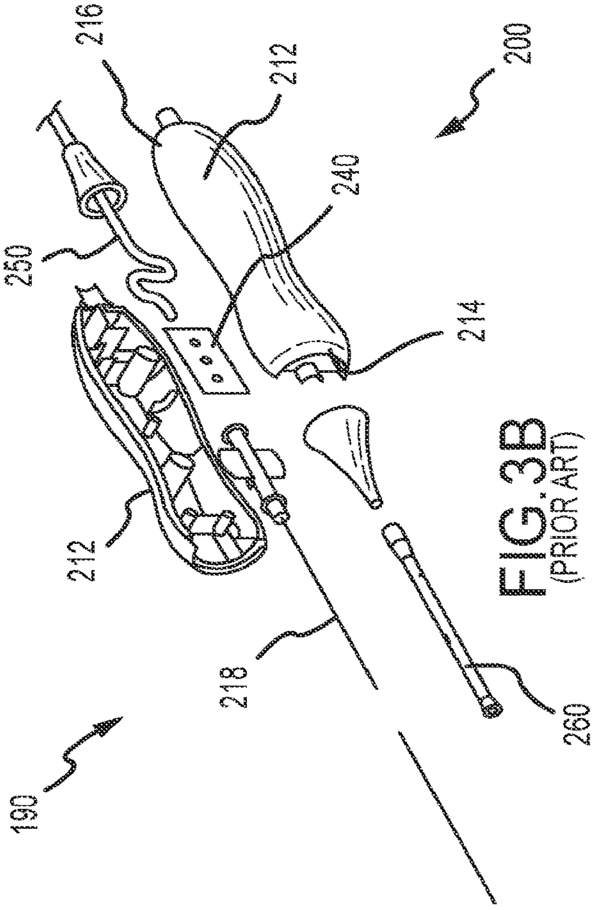
FIG.3B (PRIOR ART)
FIG. 3B is an exploded perspective view of a portion of the neuromodulation/denervation catheter of FIG. 3A.

What may be referred to as a neuromodulation or denervation catheter assembly is illustrated in FIGS. 3A and 3B and is identified by reference numeral 190. The catheter assembly 190 includes a catheter 290 and a straightening tool 260. Individual components of the catheter assembly 190 will now be addressed.

The catheter 200 of FIGS. 3A and 3B may be used in place of the neuromodulation/denervation catheter 102 shown in FIG. 1A (or any other appropriate neuromodulation and denervation system). In any case the catheter 200 includes a handle 210 (e.g., a pair of detachably connected handle sections 212), a catheter shaft 218, a printed circuit board 240 or the like within the catheter handle 210, and a generator cable 250 (e.g., electrically/operatively interconnecting the catheter 200 with a console/generator of a neuromodulation/denervation system). The catheter handle 210 may be ergonomically shaped, and includes a distal end 214 and a proximal end 216.

Figure 3C:
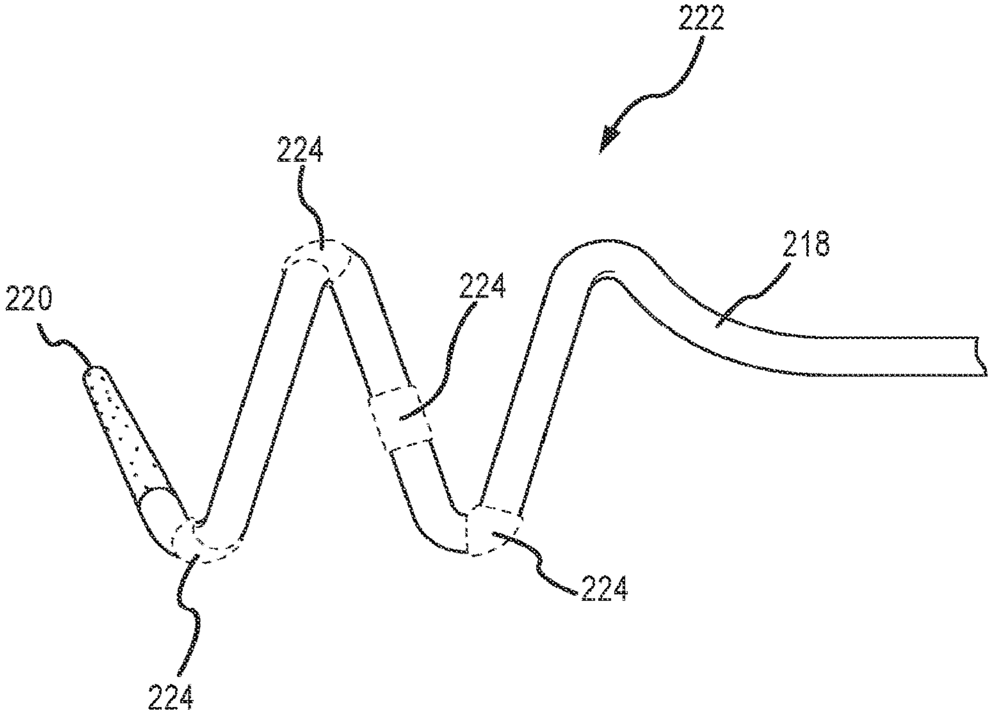
FIG. 3C is a perspective view of a distal end section of the catheter shaft for the neuromodulation/denervation catheter of FIG. 3A.

A proximal portion of the catheter shaft 218 is disposed within the catheter handle 210, with the catheter shaft 218 extending distally of the distal end 214 of the catheter handle 210. The catheter shaft 218 includes a distal end section 222 that is also shown in FIG. 3C. The distal end section 222 of the catheter shaft 218 shown in FIGS. 3A and 3C is in its deployed or expanded state. A length dimension of the distal end section 222 may be described as proceeding in a helical or spiral pattern/configuration (and thereby is curved proceeding along its length dimension).

Figure 3D:
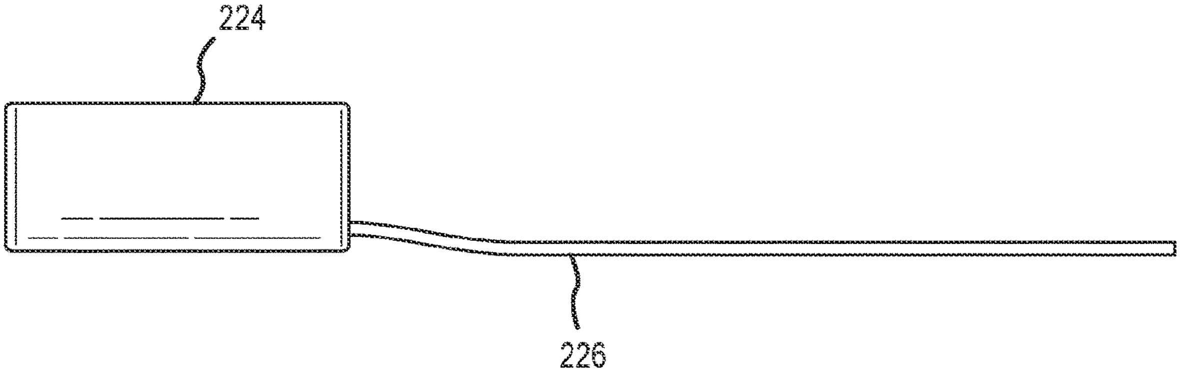
FIG. 3D is a side view of one of the electrodes and associated wiring from the distal end section of the catheter shaft for the neuromodulation/denervation catheter of FIG. 3A.
Figure 3E:
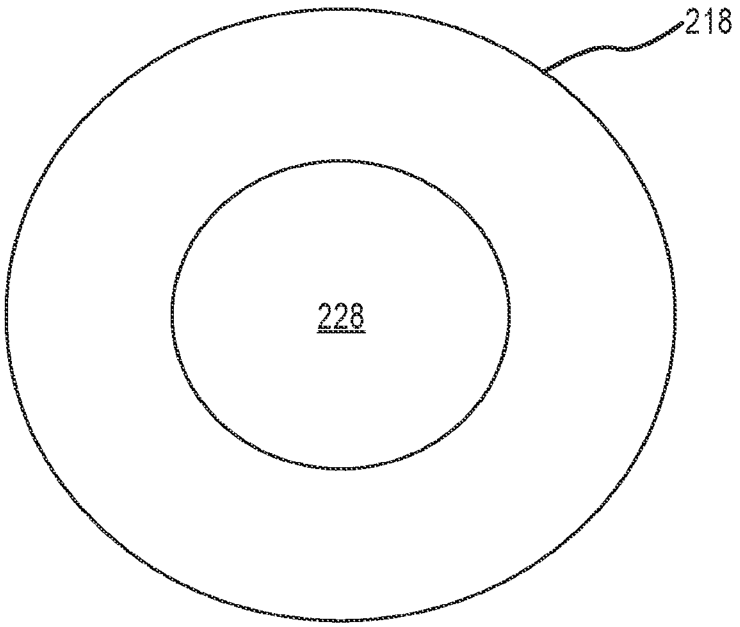
FIG. 3E is a cross-sectional schematic showing a lumen through the distal end section of the catheter shaft for the neuromodulation/denervation catheter of FIG. 3A, and through which a guidewire may be directed.
Figure 3F:
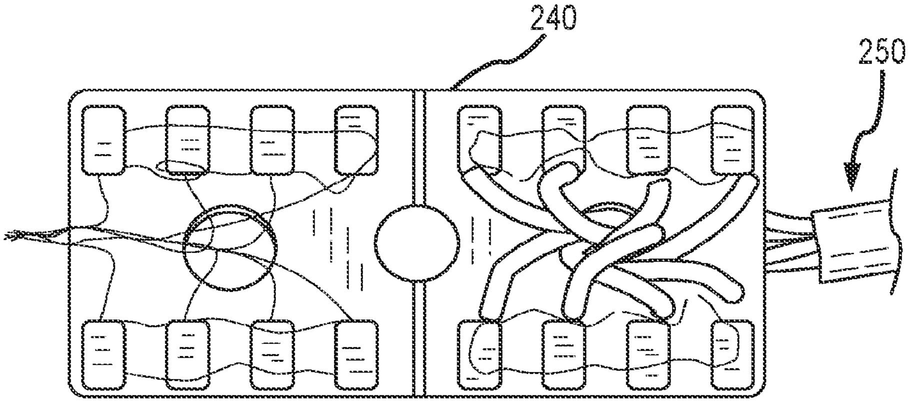
FIG. 3F is a plan view of a printed circuit board used by the neuromodulation/denervation catheter of FIG. 3A.

A plurality of electrodes 224 are spaced along the length of the distal end section 222. Each electrode 224 may be in the form of an annular band. In any case and as shown in FIG. 3D, one or more wires 226 extend from each electrode 224 back to the printed circuit board 240 that is enclosed within the catheter handle 210. In this regard, a lumen 228 is shown in FIG. 3E, and this lumen 228 extends from a distal end 220 of the catheter shaft 218 and through the catheter shaft 218 to accommodate electrically/operatively interconnecting the corresponding electrode(s) 224 with the printed circuit board 240. The printed circuit board 240 may include one or more bonding pads to provide an electrical/operative connection between the wires 226 for the electrodes 224 and the generator cable 250 (e.g., FIG. 3F). Any appropriate structure for providing an electrical/operative connection between the wires 226 for the electrodes 224 and the generator cable 250 may be utilized by the catheter handle 210.

Figure 4A:
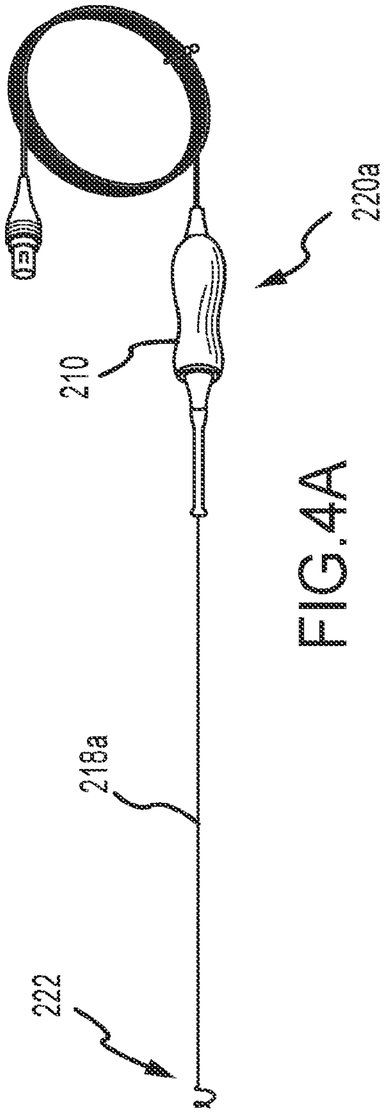
FIG. 4A is a perspective view of the neuromodulation/denervation catheter of FIGS. 3A-3F, with its catheter shaft being adapted for femoral access to the patient's vasculature.
Figure 4B:
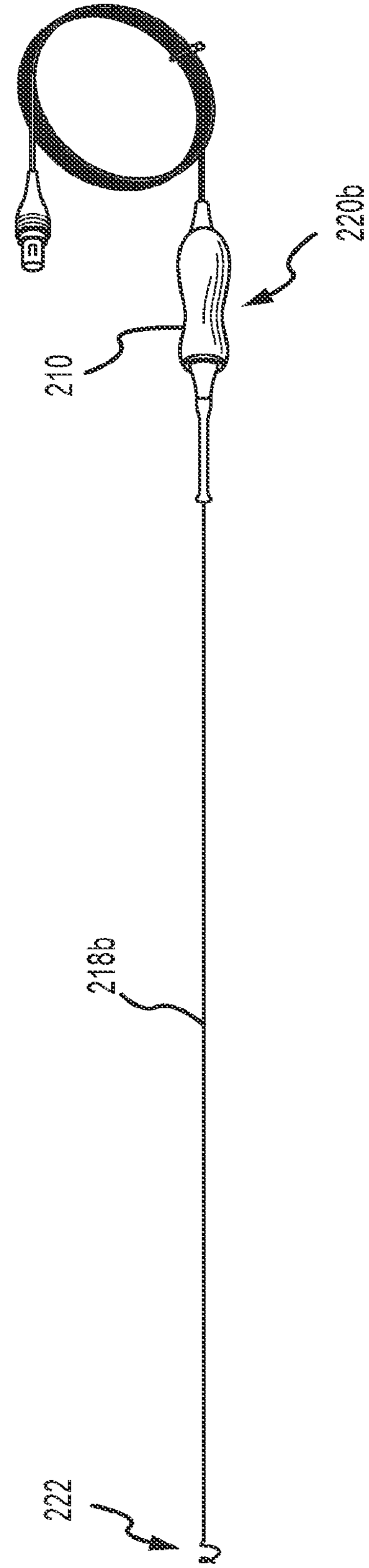
FIG. 4B is a perspective view of the neuromodulation/denervation catheter of FIGS. 3A-3F, with its catheter shaft being adapted for radial access to the patient's vasculature.

A representative configuration of the catheter assembly 190 of FIGS. 3A-3F is shown in FIG. 4A, where its neuromodulation/denervation catheter is identified by reference numeral 220*a*. The neuromodulation/denervation catheter 220*a* incorporates a working length for the catheter shaft 218*a* that has been adapted for a femoral access to a patient's vasculature. Another representative configuration of the catheter assembly 190 of FIGS. 3A-3F is shown in FIG. 4B, where its neuromodulation/denervation catheter is identified by reference numeral 220*b*. The neuromodulation/denervation catheter 220*b* incorporates a working length for the catheter shaft 218*b* that has been adapted for a radial access to a patient's vasculature. Note that the working length of the catheter shaft 218*b* (radial access) in FIG. 4B is longer than the working length of the catheter shaft 218*a* (femoral access) in FIG. 4A. Although the neuromodulation/denervation catheter 220*b* could be used to introduce the catheter shaft 218*b* through a femoral access, this would position the catheter handle 210 further from the femoral access and that could present one or more issues for an operator of the neuromodulation/denervation catheter 220*b*.

Figure 5A:
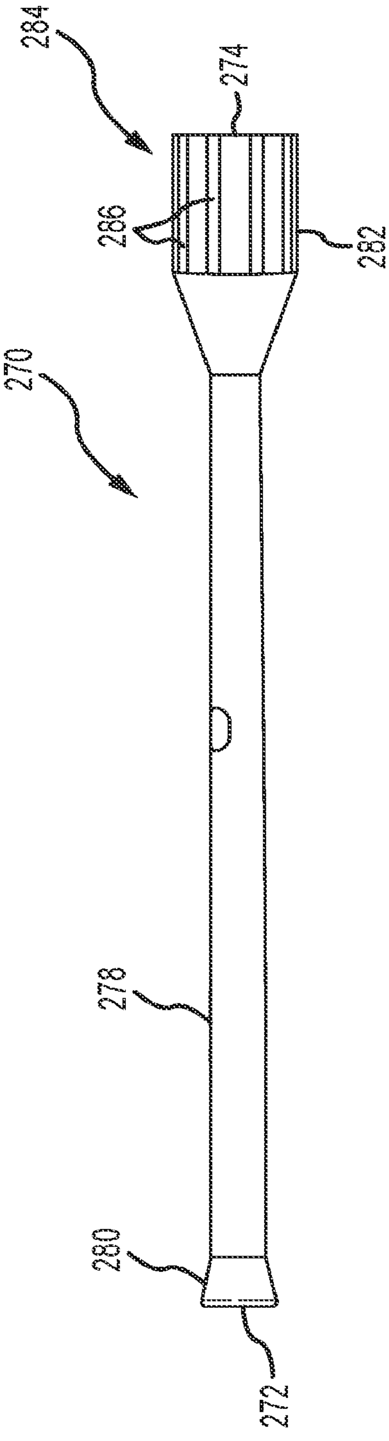
FIG. 5A is a side view of an embodiment of a multi-function catheter shaft tool.
Figure 5B:
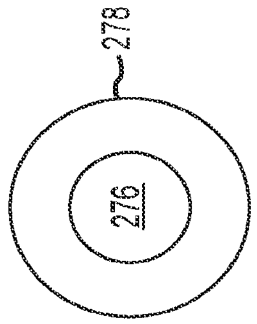
FIG. 5B illustrates a lumen that extends through the multi-function catheter shaft tool of FIG. 5A.

One embodiment of a multi-function catheter shaft tool is shown in FIGS. 5A and 5B and is identified by reference numeral 270. Hereafter, the tool 270 will be addressed in relation to the neuromodulation/denervation catheter 200 of FIGS. 3A-3F (the multi-function catheter shaft tool 270 replacing the straightening tool 260). However, it should be appreciated the multi-function catheter shaft tool 270 may be used with any appropriate catheter that includes at least one length segment for its catheter shaft where it would be beneficial to move this length segment at least toward a "straighter" profile utilizing the tool 270, and including at some point in time prior to introducing the catheter shaft into the patient's vasculature. The tool 270 could be used with a catheter having a handle (including where the tool 270 could be detachably connectable to and detachably removable from the handle), or the tool 270 could be used without any catheter handle.

The multi-function catheter shaft tool 270 includes a distal end 272 and a proximal end 274 that are spaced from one another along a length dimension of the tool 270. The tool 270 may be of any appropriate length. A lumen 276 extends through an entirety of the length of the tool 270 (e.g., from its distal end 272 to its proximal end 274). This allows the tool 270 to be disposed anywhere along the length dimension of the catheter shaft 218, including where the catheter shaft 218 extends proximally of the tool 270. The cross-sectional shape of the lumen 276 may be constant throughout the length of the tool 270 although such is not required. The lumen 276 merely needs to accommodate passage of the catheter shaft 218 therethrough, and as such at least a portion of the lumen 276 need not necessarily be defined by an annular inner wall along the entirety of its length.

The multi-function catheter shaft tool 270 includes a catheter shaft straightener 278 and a catheter shaft actuator 282. The catheter shaft actuator 282 defines a proximal end section of the tool 270 in the illustrated embodiment, although it may be disposed anywhere along the length of the tool 270 so long as a sufficient length of the catheter shaft straightener 278 extends distally from the catheter shaft actuator 282. The catheter shaft straightener 278 extends distally from a distal end of the catheter shaft actuator 282 to the distal end 272 of the tool 270 in the illustrated embodiment. The catheter shaft straightener 278 may be of any appropriate length.

The catheter shaft straightener 278 may include a flared distal end section 280. An outer diameter of the distal end section 280 may progressively increase proceeding in the direction of the distal end 272 of the multi-function catheter shaft tool 270 (as may the inner diameter of the lumen 276 along the flared distal end section 280). A remainder of the catheter shaft straightener 279 may be of a constant outer diameter (e.g., a smaller outer diameter compared to a maximum outer diameter of the distal end section 280). The distal end section 280 could also be of the same diameter as the remainder of the catheter shaft straightener 278, but could be "softer" than a remainder of the catheter shaft straightener 278 (e.g., for enhanced manipulation of the distal end section 280, for instance when loading a guidewire into a catheter shaft). For instance, a durometer rating of the distal end section 280 (whether flared or not) may be less than a durometer rating of the remainder of the catheter shaft straightener 278 (e.g., the distal end section 280 could have a lower rating on the Shore Hardness Scale compared to a remainder of the catheter shaft straightener 278). The catheter shaft straightener 278 may be formed from any appropriate material or combination of materials, for instance silicone (e.g., to reduce a potential for damaging the electrodes 224 incorporated by the distal end section 222 of the catheter shaft 218).

The catheter shaft actuator 282 may include a grip or engagement section 284 having a larger outer diameter than an outer diameter of the catheter shaft straightener 278, for instance so as to be sufficiently sized for a user to exert a force on the catheter shaft actuator 282 by grasping the engagement section 284. The outer perimeter of the engagement section 284 may include a plurality of circumferentially-spaced segments 284 for facilitating engagement by a user. Any appropriate material or combination of materials may be used to fabricate/form the catheter shaft actuator 282. In one embodiment at least a portion of the catheter shaft actuator 282 is more rigid than the catheter shaft straightener 282 (e.g., at least part of the catheter shaft actuator 282 may have a higher durometer rating than the catheter shaft straightener 278). A distal section 288 of the catheter shaft actuator 282 extends distally from the engagement section 284, and may do so in converging relation to the lumen 276 proceeding in the direction of the catheter shaft straightener 278. In any case, at least part of the catheter shaft straightener 278 extends distally from a distal end of the catheter shaft actuator 282. The catheter shaft straightener 278 and catheter shaft actuator 282 are appropriately interconnected (e.g., fixed or joined) such that the catheter shaft straightener 278 and catheter shaft actuator 282 collectively rotate about a centerline of the lumen 276

(e.g., when torqueing the catheter shaft 218), when advancing the catheter shaft 218 within a patient's vasculature, or both.

The catheter shaft actuator 282 may include an appropriate clamping mechanism that may be actuated between a released configuration and a clamping configuration. For instance, the multi-function catheter shaft tool 270 could include a clamping actuator 390 and clamp 392 of the type discussed below in relation to FIGS. 8A-8D, including where the actuator 390 is disposed on an exterior of the catheter shaft actuator 282 (or any other appropriate location). The clamping actuator 444 and corresponding clamp 446, discussed below in relation to FIGS. 9A-9D, could also be utilized by the multi-function catheter shaft tool 270. In any case disposing the clamping mechanism of the multi-function catheter shaft tool 270 in its released configuration allows the tool 270 to be repositioned along the length of the catheter shaft 218, whereas disposing the clamping mechanism of the multi-function catheter shaft tool 270 in its clamping configuration allows the tool 270 to suitably engage (e.g., clamp onto) the exterior of the catheter shaft 218 such that exerting a rotary movement on the catheter shaft actuator 282 may be used to torque the catheter shaft 218, such that an at least generally axially-directed force may be exerted on the catheter shaft actuator 282 (e.g., pushing or pulling) to advance the catheter shaft 218 relative to the patient's vasculature, or both.

The multi-function catheter shaft tool 270 of FIGS. 5A-5B provides two discrete functions—"straightening" (e.g., distal end section 222 of the catheter shaft 218) and movement of the catheter shaft 218 (e.g. torqueing and/or advancement relative to the patient's vasculature). The clamping mechanism of the multi-function catheter shaft tool 270 may be disposed in its released configuration such that the tool 270 may be advanced along the length of the catheter shaft 218 and in the direction of its distal end 214. The flared distal end section 280 of the catheter shaft straightener 278 should facilitate entry of the distal end section 222 of the catheter 218 (initially a proximal end of the distal end section 222) into the catheter shaft straightener 278. In this regard, the wall thickness of the flared distal end section 280 may be less than the wall thickness of the remainder of the catheter shaft straightener 278. Advancing the tool 270 in the distal direction should reduce the profile of the distal end section 222 of the catheter shaft 218 as it enters the catheter shaft straightener 278 (e.g., inwardly compress or move the distal end section 222 at least toward a "straighter" profile in relation to its length dimension). The distal end 272 of the tool 270 may be disposed at/proximate to the distal end 214 of the catheter shaft 218. At this time, the clamping mechanism of the multi-function catheter shaft tool 270 may be actuated into its clamping configuration, if desired. In any case, a proximal end of a guidewire (e.g., guidewire 140) may be directed into the lumen 228 that intersects with the distal end 220 of the catheter shaft 218. The guidewire may be advanced proximally a sufficient distance relative to the tool 270/catheter shaft 218, at which time the clamping mechanism of the multi-function catheter shaft tool 270 may be actuated to its released configuration such that the multi-function catheter shaft tool 270 may be advanced proximally along and relative to the catheter shaft 218 to an appropriate location.

The multi-function catheter shaft tool 270 may also be used to torque the catheter shaft 218 and/or to advance the catheter shaft 218 relative to the patient's vasculature. The clamping mechanism of the multi-function catheter shaft tool 270 may be actuated into its released configuration such that the multi-function catheter shaft tool 270 may be advanced along and relative to the catheter shaft 218 to a desired location (e.g., in proximity to the access to the patient's vasculature, whether using a femoral access, a radial access, or any other vasculature access). Thereafter, the clamping mechanism of the multi-function catheter shaft tool 270 may be actuated into its clamping configuration such that the clamping mechanism of the multi-function catheter shaft tool 270 engages an exterior of the catheter shaft 218, where subsequent rotation of the catheter shaft actuator 282 (e.g., about a center line of the lumen 276) will correspondingly rotate the catheter shaft 218 about its length dimension and where advancement of the catheter shaft actuator 282 (e.g., by pushing or pulling on the catheter shaft actuator 282) will correspondingly advance the catheter shaft relative to the patient's vasculature. As the catheter shaft straightener 278 is appropriately fixed relative to the catheter shaft actuator 282, this movement of the catheter shaft actuator 282 will also correspondingly move the catheter shaft straightener 278.

Another embodiment of a multi-function catheter shaft tool is illustrated in FIGS. 6A-7C and is identified by reference numeral 290. Hereafter, the tool 290 will be addressed in relation to the neuromodulation/denervation catheter 200 of FIGS. 3A-3F (the multi-function catheter shaft tool 290 replacing the straightening tool 260). However, it should be appreciated the multi-function catheter shaft tool 290 may be used with any appropriate catheter that includes at least one length segment for its catheter shaft where it would be beneficial to move this length segment at least toward a "straighter" profile utilizing the tool 290, and including at some point in time prior to introducing the catheter shaft into the patient's vasculature. The tool 290 could be used with a catheter having a handle (including where the tool 290 could be detachably connectable to and detachably removable from the handle), or the tool 290 could be used without any catheter handle.

Figure 6A:
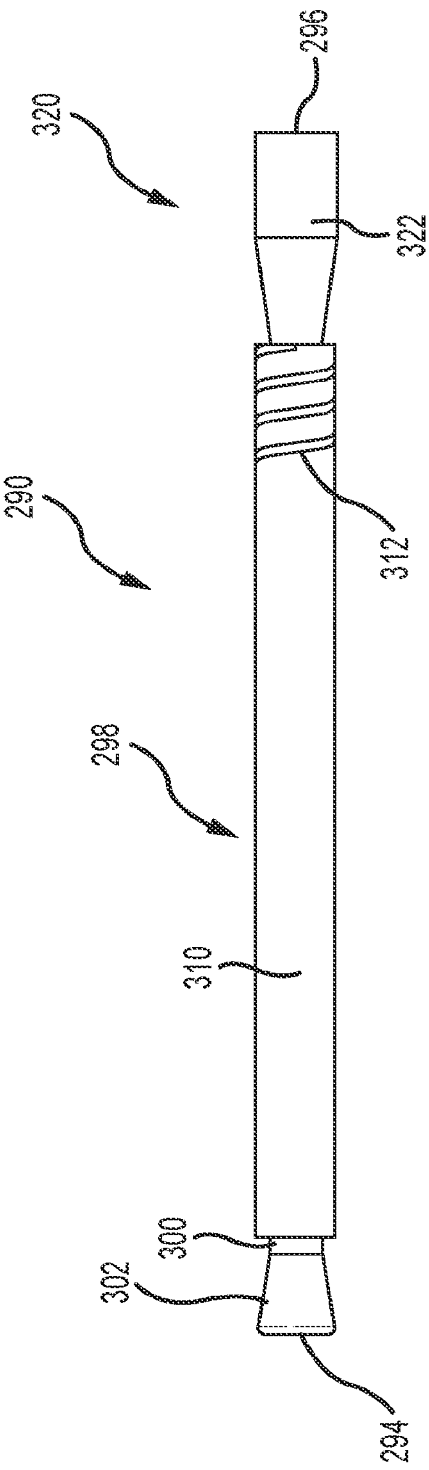
FIG. 6A is a side view of another embodiment of part of a multi-function catheter shaft tool.
Figure 6B:
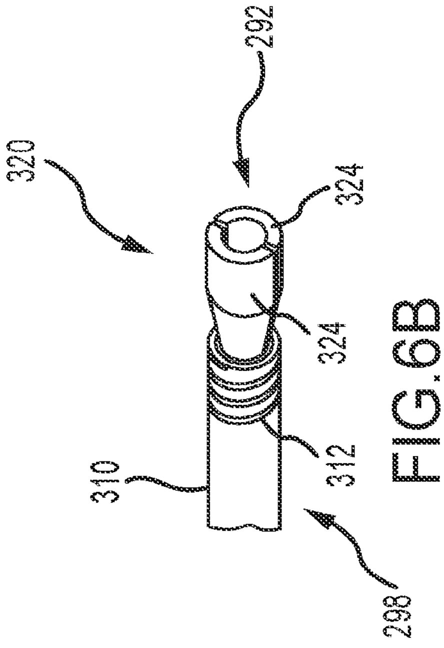
FIG. 6B is a perspective view of a proximal end section of the part of the multi-function catheter shaft tool shown in FIG. 6A.
Figure 6C:
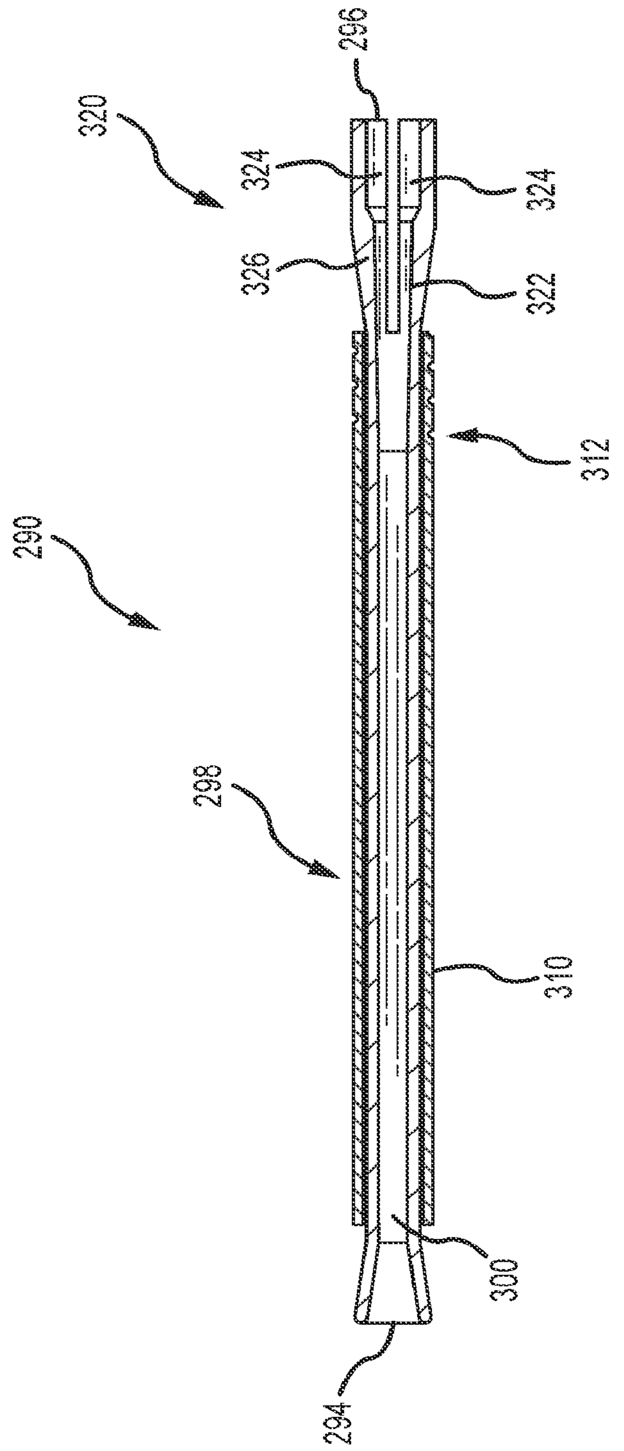
FIG. 6C is a cutaway, side view of the part of the multi-function catheter shaft tool shown in FIG. 6A.

The multi-function catheter shaft tool 290 includes a distal end 294 and a proximal end 296 that are shown in FIGS. 6A and 6C. An interior lumen 292 extends between this distal end 294 and proximal end 296. The distal end 294 is the distalmost end for the entirety of the tool 290, whereas the proximal end 296 is disposed at an intermediate location along a length dimension of the tool 290 and as will be addressed in more detail below.

There are two main components/subassemblies of the multi-function catheter shaft tool 290—a catheter shaft straightener 298 and a catheter shaft actuator 320. Details of the catheter shaft straightener 290 will be addressed in relation to FIGS. 6A-6C, which also illustrate a clamping section 322 of the catheter shaft actuator 320. The above-noted distal end 294 is disposed at the distal end of the catheter shaft straightener 290, while the above-noted proximal end 296 is disposed at the distal end of the clamping section 322 of the catheter shaft actuator 320.

The catheter shaft straightener 298 includes a liner 300 and an outer housing or tube 310. The liner 300 extends distally beyond a distal end of the outer housing 310, and may include a flared distal end section 302, which may be in accord with the distal end section 280 discussed above. An outer diameter of the distal end section 302 may progressively increase proceeding in the direction of the distal end 294 of the tool 290. A remainder of the liner 300 may be of a constant outer diameter (e.g., a smaller outer diameter compared to a maximum outer diameter of the distal end section 302). The liner 300 may be formed from any appropriate material or combination of materials, for instance silicone (e.g., to reduce a potential for damaging the electrodes 224 incorporated by the distal end section 222 of the catheter shaft 218).

The outer housing or tube 310 of the catheter shaft straightener 298 is disposed circumferentially about the liner 300 along a substantial portion of a length of the liner 300. The distal end of the outer housing 310 may be located adjacent to the flared distal end section 302 of the liner 300. External threads 312 are formed on an exterior of the outer housing 310. These threads 312 may be disposed on a proximal end section of the exterior of the outer housing 310.

A proximal end of the liner 300 may terminate within an interior location along the length of the outer housing 310. In any case, the proximal end of the liner 300 may be appropriately fixed or secured to the clamping section 322 of the catheter shaft actuator 320. At least one deflectable section 324 is incorporated on a proximal end section of the clamping section 322. A pair of deflectable sections 324 are disposed in opposing relation to one another in the illustrated embodiment, with a pair of opposing slots being disposed between this pair of deflectable sections 324. A cover 326 may be disposed over/about the liner 300 and clamping section 322 along their respective lengths.

Each of the liner 300 and the outer housing 310 may be formed from any appropriate material or combination of materials. However, the outer housing 310 may be more rigid than the liner 300 (e.g., for reducing the potential for damage to the electrodes 224 on the distal end section 222 of the catheter shaft 218). For instance, the liner 300 may formed from silicone or other suitably "soft" materials. The outer housing 310 may be characterized as having a first hardness, the liner 300 may be characterized as having a second hardness, with the second hardness being less than the first hardness, and that may facilitate reducing the profile of the distal end section 222 of the catheter shaft 218 while reducing the potential for damaging the electrodes 224 on the distal end section 222 of the catheter shaft 218 while introducing the distal end section 222 into the catheter shaft straightener 298 (e.g., the outer housing 310 may have a higher durometer rating than the liner 300).

Figure 6D:
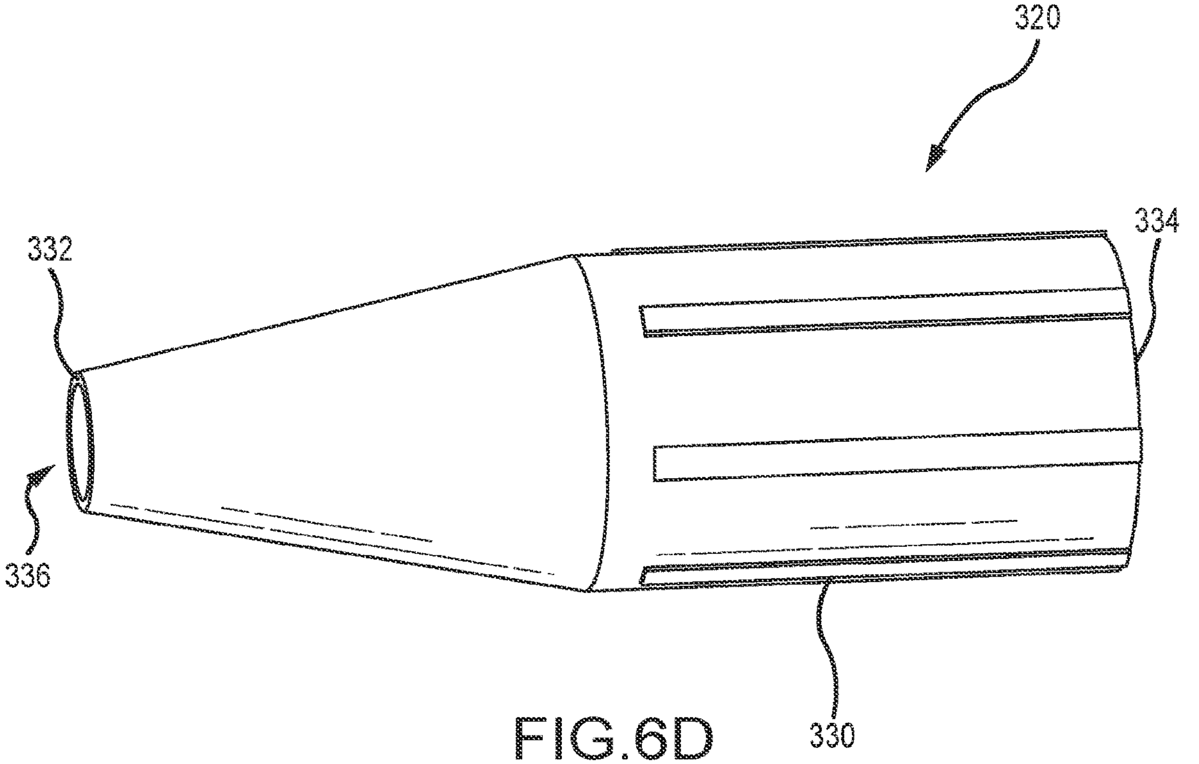
FIG. 6D is a perspective side view of a cap that is used in combination with the structure of FIGS. 6A-6C to define a multi-function catheter shaft tool.
Figure 6E:
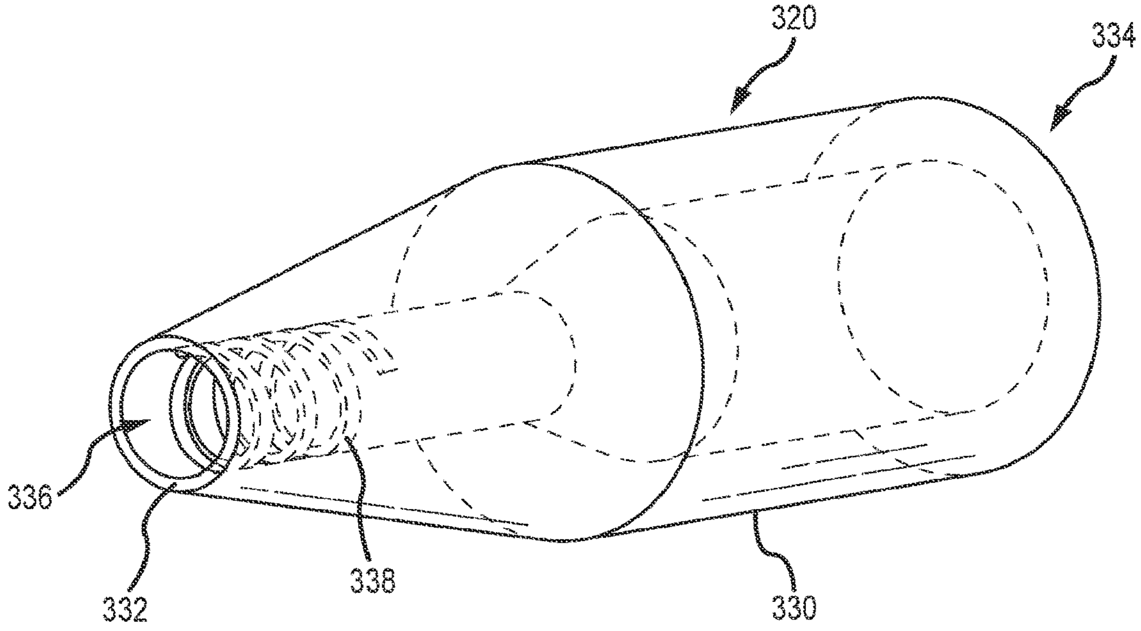
FIG. 6E is a transparent perspective side view of the cap shown in FIG. 6D.
Figure 7A:
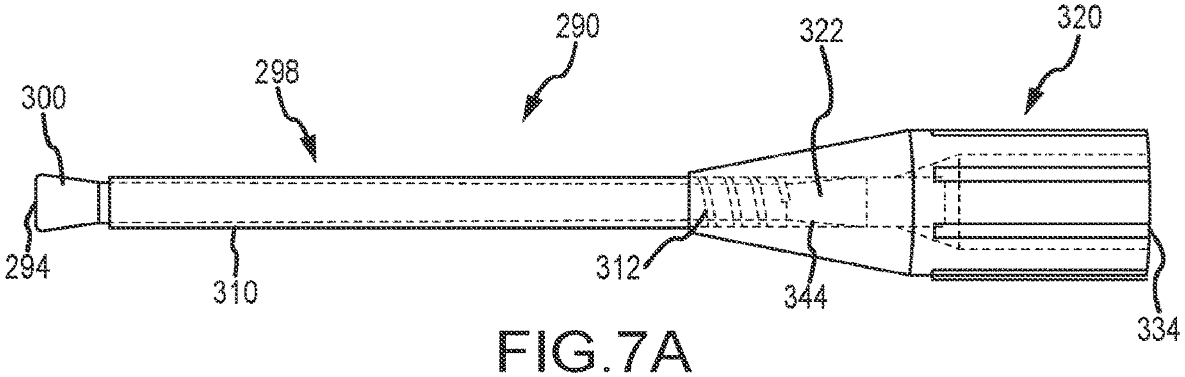
FIG. 7A is a transparent side view of the assembled components shown in FIG. 6A-6E to define the multi-function catheter shaft tool.
Figure 7B:
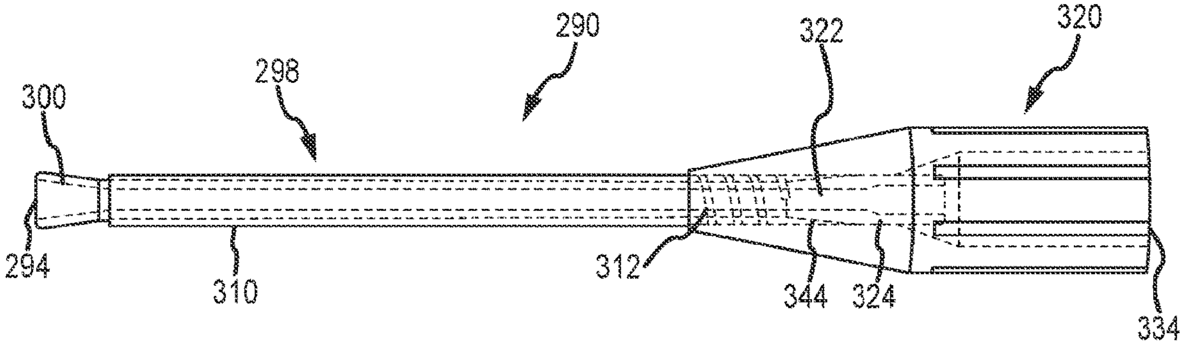
FIG. 7B is another transparent side view of the assembled components shown in FIG. 6A-6E to define the multi-function catheter shaft tool.
Figure 7C:
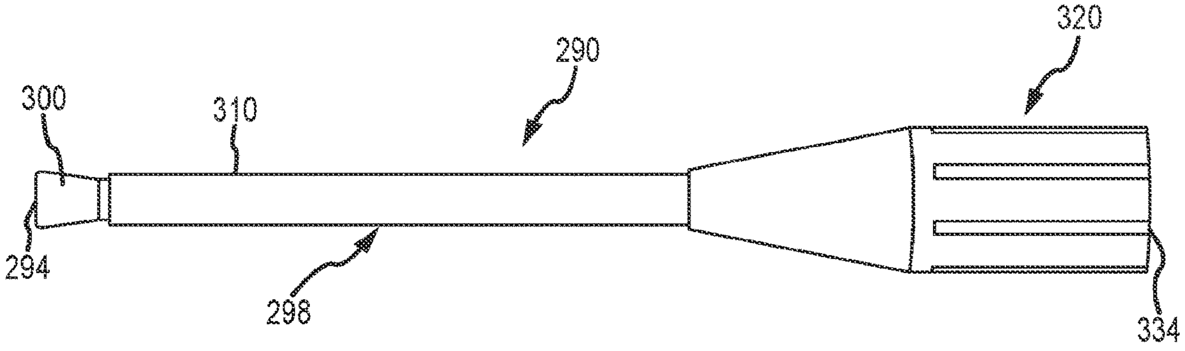
FIG. 7C is a side view of the assembled components shown in FIG. 6A-6E to define the multi-function catheter shaft tool.

FIGS. 6D and 6E present views of a body or cap 330 for the catheter shaft actuator 320. As the cap 330 may be used to change the catheter shaft actuator 320 between a clamping configuration and a released configuration (relative to the catheter shaft 218), as well as for torqueing and/or the catheter shaft 218, the cap 300 may also be referred to as a "catheter shaft actuator 330." In any case, the cap 330 includes a distal end 322 and a proximal end 334 that are spaced from one another along a length dimension of the cap 330. A passage, open space, or pathway 336 extends from the distal end 332 of the cap 330 to the proximal end 334 of the cap 330. Internal threads 338 are formed about the passage 336 of the cap 330, for instance along a distal end section of the passage 336. An activating surface 340 is also disposed within the interior of the cap 330, interfaces with the passage 336, and cooperates with the clamping section 322 to dispose the catheter shaft actuator 320 into its clamping configuration. Based upon the foregoing it should be appreciated that the multi-function catheter shaft tool 290 may be mounted on the catheter shaft 218, with the catheter shaft 218 extending entirely through the length of the tool 290 (including proximally).

A proximal end section of the outer housing 310 of the catheter shaft straightener 298 may be directed into the passage 336 at the distal end 332 of the cap 330 (which also directs at least a proximal end portion of the clamping section 322 of the catheter shaft actuator 320 into this passage 336 as well). Rotation of the cap 330 (catheter shaft actuator 320) relative to the outer housing 310 (catheter shaft straightener 298) engages the interior threads 338 of the cap 330 with the external threads 312 of the outer housing 310, to thereby couple the catheter shaft actuator 280 to the catheter shaft straightener 298. The initial threaded engagement between the cap 330 and the outer housing 310 may allow for coupling of the catheter shaft actuator 320 and the catheter shaft straightener 298 without activating the deflectable sections 324 of the clamping section 322 (e.g., the deflectable sections 324 of the clamping section 322 may be spaced from or otherwise may not be exerting a clamping force on the catheter shaft 218 at this time). This again will be referred to as a "released configuration" for the catheter shaft actuator 320. It should be appreciated that the catheter shaft actuator 320 is also in its released configuration when the cap 330 is not threadably engaged with the outer housing 310. When a threaded engagement has been established between the cap 330 and the outer housing 310, continued rotation of the cap 330 relative to the outer housing 310 will axially advance the cap 330 in the direction of the distal end 294 of the tool 290, which will eventually cause the activating surface 340 of the cap 330 to exert an inwardly-directed force on the deflectable sections 324 of the clamping section 322, so as to dispose the clamping section 322 in the clamping configuration where at least the deflectable sections 324 are clamped against an exterior of the catheter shaft 218.

The multi-function catheter shaft tool 290 of FIGS. 6A-7C provides two discrete functions—"straightening" (e.g., distal end section 222 of the catheter shaft 218) and movement of the catheter shaft 218 (e.g. torqueing and/or advancement relative to the patient's vasculature). The catheter shaft actuator 320 may be disposed in its released configuration such that the tool 290 may be advanced along the length of the catheter shaft 218 and in the direction of its distal end 214 of the catheter shaft 218. The flared distal end section 302 of the liner 300 should facilitate entry of the distal end section 222 of the catheter 218 (initially a proximal end of the distal end section 222) into the liner 300. In this regard, the wall thickness of the flared distal end section 302 may be less than the wall thickness of the remainder of the liner 300. Advancing the tool 290 in a distal direction should reduce the profile of the distal end section 222 of the catheter shaft 218 as it enters the catheter shaft straightener 298 (e.g., inwardly compress or move the distal end section 222 at least toward a "straighter" profile in relation to its length dimension). The distal end 294 of the tool 290 may be disposed at/proximate to the distal end 214 of the catheter shaft 218. At this time, the catheter shaft actuator 320 may be actuated into its clamping configuration in the above-manner, if desired. In any case, a proximal end of a guidewire (e.g., guidewire 140) may be directed into the lumen 228 that intersects with the distal end 220 of the catheter shaft 218. The guidewire may be advanced proximally a sufficient distance relative to the tool 290/catheter shaft 218, at which time the catheter shaft actuator 320 may be actuated to its released configuration such that the multi-function catheter shaft tool 290 may be advanced proximally along and relative to the catheter shaft 218 to an appropriate location.

The multi-function catheter shaft tool 290 may also be used to torque the catheter shaft 218 and/or to advance the catheter shaft 218 relative to the patient's vasculature. The catheter shaft actuator 320 may be actuated into its released configuration such that the multi-function catheter shaft tool 290 may be advanced along and relative to the catheter shaft 218 to a desired location (e.g., in proximity to the access to the patient's vasculature, whether using a femoral access, a radial access, or any other vasculature access). Thereafter, the catheter shaft actuator 320 may be actuated into its clamping configuration such that catheter shaft actuator 320 (more specifically the deflectable sections 324 of its clamping section 322) engages an exterior of the catheter shaft 218. At this time, rotation of the catheter shaft actuator 320 (e.g., about a centerline of the lumen 292) will correspondingly rotate the catheter shaft 218 about its length dimension. As the catheter shaft straightener 298 is appropriately fixed relative to the catheter shaft actuator 320, this rotation of the catheter shaft actuator 320 will also correspondingly rotate the catheter shaft straightener 298. Advancement of the catheter shaft actuator 320 (e.g., by pushing or pulling on the catheter shaft actuator 320) will advance the catheter shaft 218 relative to the patient's vasculature in a corresponding direction (and will similarly advance the catheter shaft straightener 298).

An embodiment of a catheter assembly is illustrated in FIGS. 8A-8D and is identified by reference numeral 350. There are two primary components/subassemblies of the catheter assembly 350—a catheter 360 and a catheter shaft actuator 370. The catheter 360 may correspond with the above-noted neuromodulation/denervation catheter 200, but the catheter 360 may be of any appropriate type/configuration and that provides any appropriate function or combination of functions when disposed in a patient's vasculature (e.g., diagnostic, therapeutic, neuromodulation, denervation).

The catheter 360 includes a handle 362 and a catheter shaft 364 that extends distally from a distal end of the catheter handle 362. The catheter shaft 364 may extend at least into the distal end of the catheter shaft handle 362, and the catheter shaft handle 362 may engage the catheter shaft 364 in a manner that allows the catheter shaft handle 362 to be used to move the catheter shaft 364 (e.g., torque and/or advance the catheter shaft 364 relative to the patient's vasculature) in a manner that will be discussed in more detail below (e.g. the catheter shaft 364 may be appropriately anchored/fixed relative to the catheter handle 362). A generator connector 366 extends from a proximal end of the catheter handle 360.

The catheter shaft actuator 370 includes a body 372 having a distal end 374 and a proximal end 376 that are spaced from one another along a length dimension of the body 372. As the body 372 may be used to move the catheter shaft 218 in a manner that will be discussed in more detail below, the body 372 may also be referred to as a "catheter shaft actuator 372." The body 372 may be fabricated in any manner, for instance in separate halves.

An annular first tube 394 extends from the distal end 374 of the body 372. This first tube 394 may be used to reduce the potential for kinking of the catheter shaft 218 when being torqued and/or advanced (e.g., relative to the patient's vasculature) by the catheter shaft actuator 370. An annular second tube 398 extends from the proximal end 376 of the body 372. The first tube 394 includes an annular first lumen 396 that extends to a passage defined by an annular first cylindrical section 380 within the interior of the body 372. The second tube 398 includes an annular second lumen 400 that extends to a passage defined by an annular second cylindrical section 382 within the interior of the body 372. The first cylindrical section 380 and the second cylindrical section 382 are axially aligned but are spaced from one another within the interior of the body 372. A clamp 392 is disposed in the space between the first cylindrical section 380 and the second cylindrical section 382 within the interior of the body 372. An actuator 390 is disposed on an exterior of the body 372 and is movable between first and second positions to dispose the clamp in a released configuration and a clamping configuration, respectively. As such, the actuator 390 may also be referred to as a "clamping actuator 390."

Disposing the clamping actuator 390 in its released configuration (by movement of the actuator 390, to produce a corresponding movement of the clamp 392) allows the catheter shaft actuator 370 to be advanced along and relative to the catheter shaft 364 to a desired location (e.g., in proximity to the access to the patient's vasculature, whether using a femoral access, a radial access, or any other vasculature access). Disposing the clamping actuator 390 in its clamping configuration (by movement of the actuator 390, to produce a corresponding movement of the clamp 392) causes the clamp 392 to engage an exterior of the catheter shaft 364 such that rotation of the catheter shaft actuator 370 (e.g., by engagement of the body 372) will correspondingly rotate the catheter shaft 364 about its length dimension, and such that advancement of the catheter shaft actuator 370 (e.g., by engagement of and pushing or pulling on the body 372) will advance the catheter shaft 364 along the patient's vasculature in the corresponding direction. The noted "rotation" may be described as being about a centerline through the first lumen 396 of the first tube 394, the passage defined by the first cylindrical section 380, the passage defined by the second cylindrical section 382, and the second lumen 400 of the second tube 398.

Figure 8A:
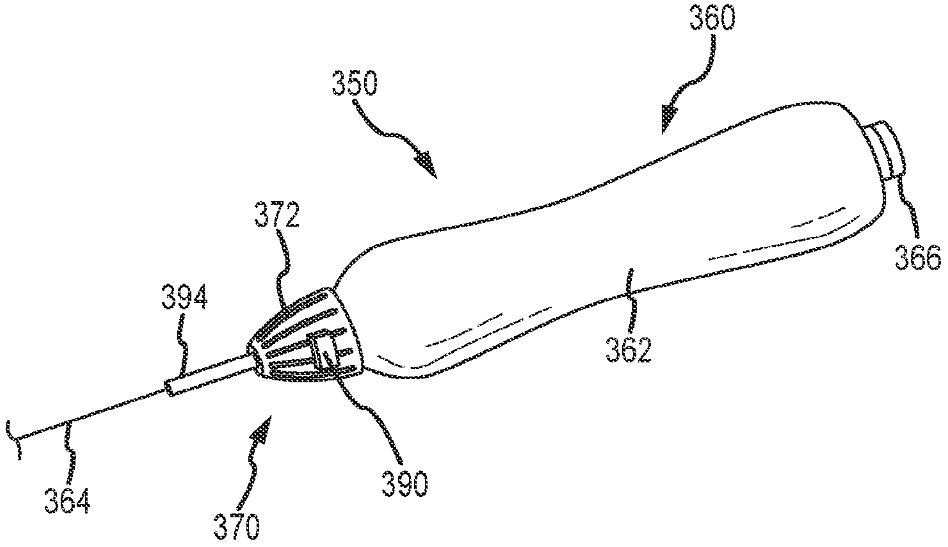
FIG. 8A is a perspective view of an embodiment of a catheter assembly that utilizes both a catheter handle and a separate catheter shaft actuator, and with the catheter shaft actuator being in a first position relative to the catheter handle.

The catheter shaft actuator 370 may be disposed such that its second tube 398 extends within the distal end of the catheter handle 362 and as shown in FIG. 8A. Disposing the clamping actuator 390 in its clamping configuration (by movement of the actuator 390, to produce a corresponding movement of the clamp 392) may maintain the catheter shaft actuator 370 in a fixed position relative to the catheter shaft handle 364 at this time. Features could also be incorporated to actually detachably connect the catheter handle 362 and the catheter shaft actuator 370. In any case and in the FIG. 8A configuration, the catheter shaft handle 364 may be used to torque the catheter shaft 364 (e.g., by a user engaging the catheter handle 362 and rotating the same about the length dimension of the catheter shaft 364), to advance the catheter shaft 364 (e.g., by a user engaging the catheter handle 362 and pushing or pulling on the catheter handle 364 to advance the catheter shaft 364 along the patient's vasculature in a corresponding direction), or both. For instance, the configuration shown in FIG. 8A could be for a radial access to the patient's vasculature (or any other vasculature access). Having the clamping actuator 390 in its clamping configuration when disposed in the FIG. 8A configuration (even when the user is engaging the catheter handle 362 to exert a force on the catheter shaft 364), however, may also further facilitate the desired movement of the catheter shaft 364, as the catheter handle 362 and the clamp 392 would be engaging the catheter shaft 364 at spaced locations and each of these engagements alone should accommodate the desired movement of the catheter shaft 364 (whether via manipulation of the catheter shaft actuator 370 or the catheter handle 362).

Figure 8B:
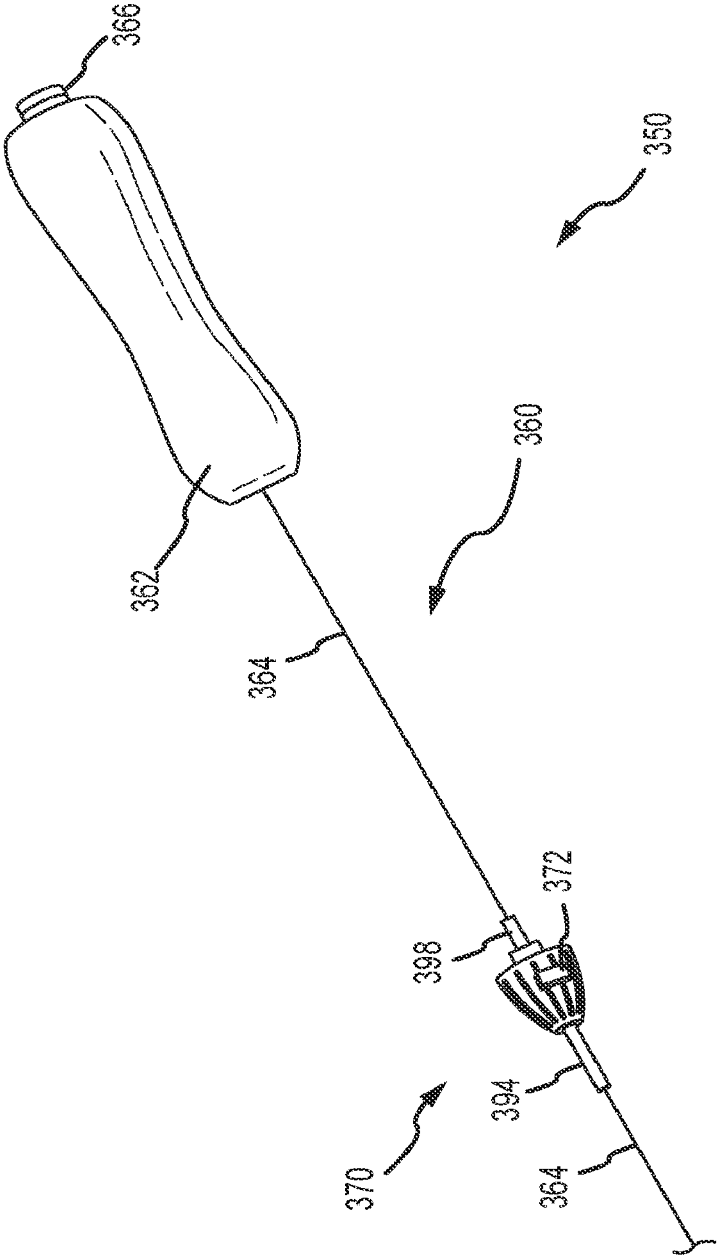
FIG. 8B is a perspective view of the catheter assembly of FIG. 8A, with the catheter shaft actuator being in a second position relative to the catheter handle.
Figure 8C:
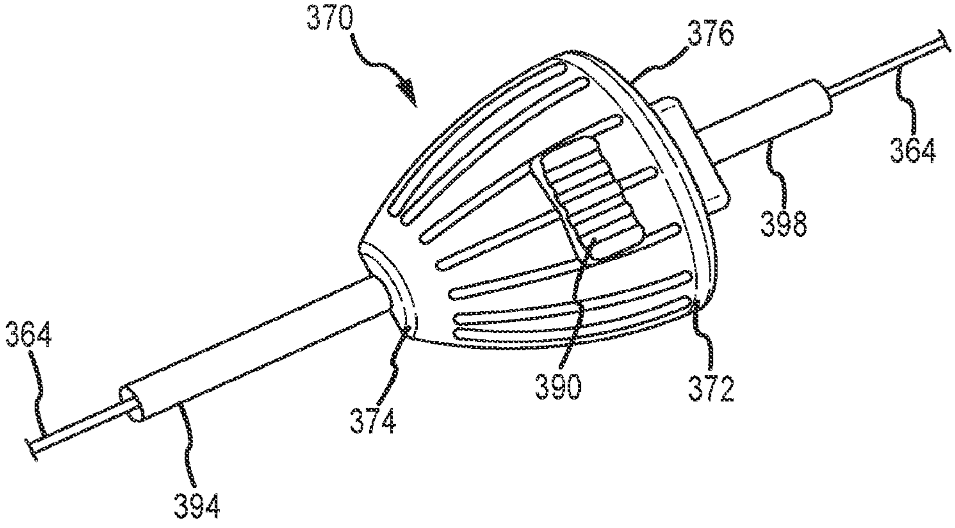
FIG. 8C is an enlarged, perspective view of a section of the catheter shaft actuator for the catheter assembly of FIG. 8A.
Figure 8D:
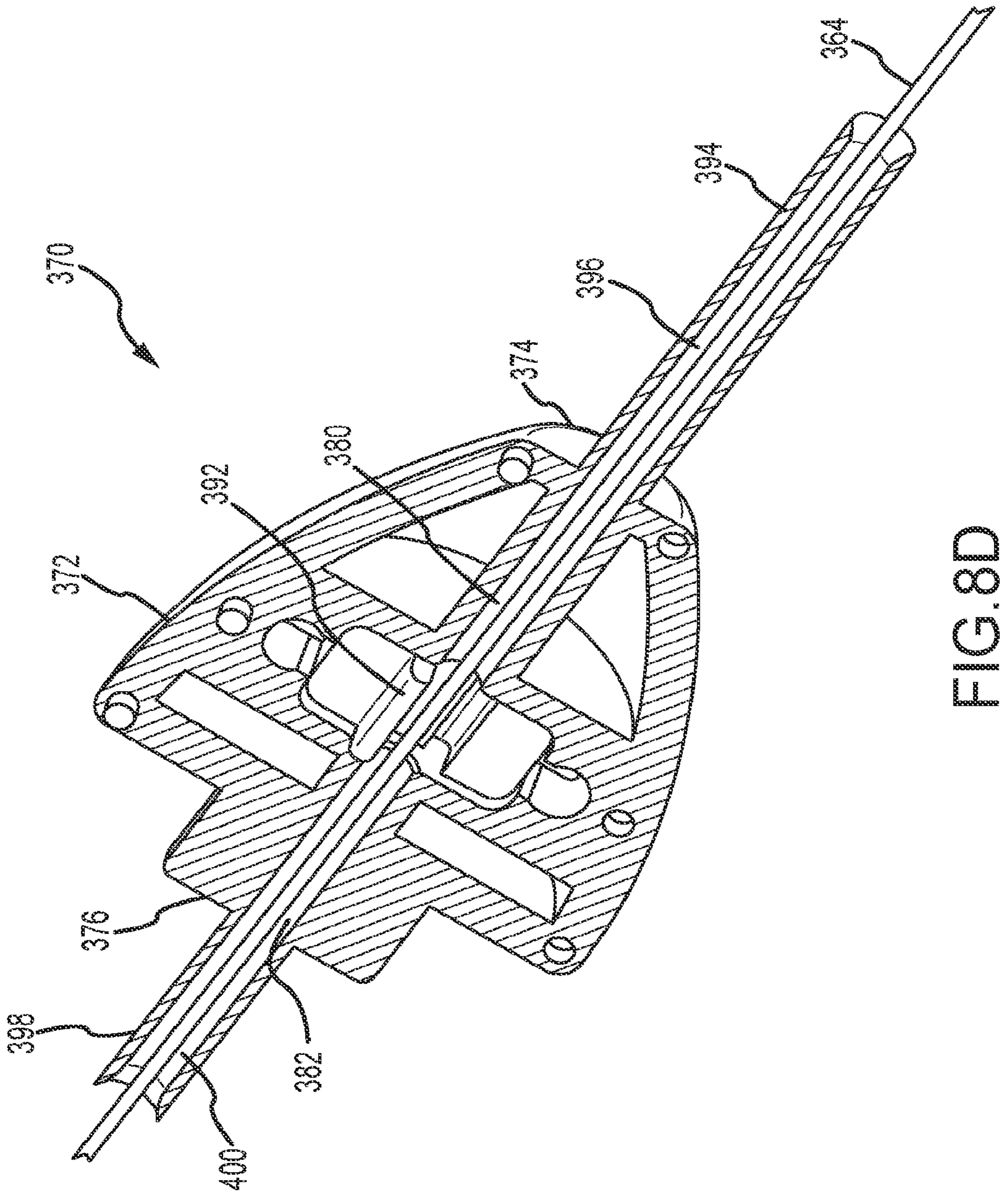
FIG. 8D is an enlarged, cutaway view of the catheter shaft actuator for the catheter assembly of FIG. 8A.
Figure 9A:
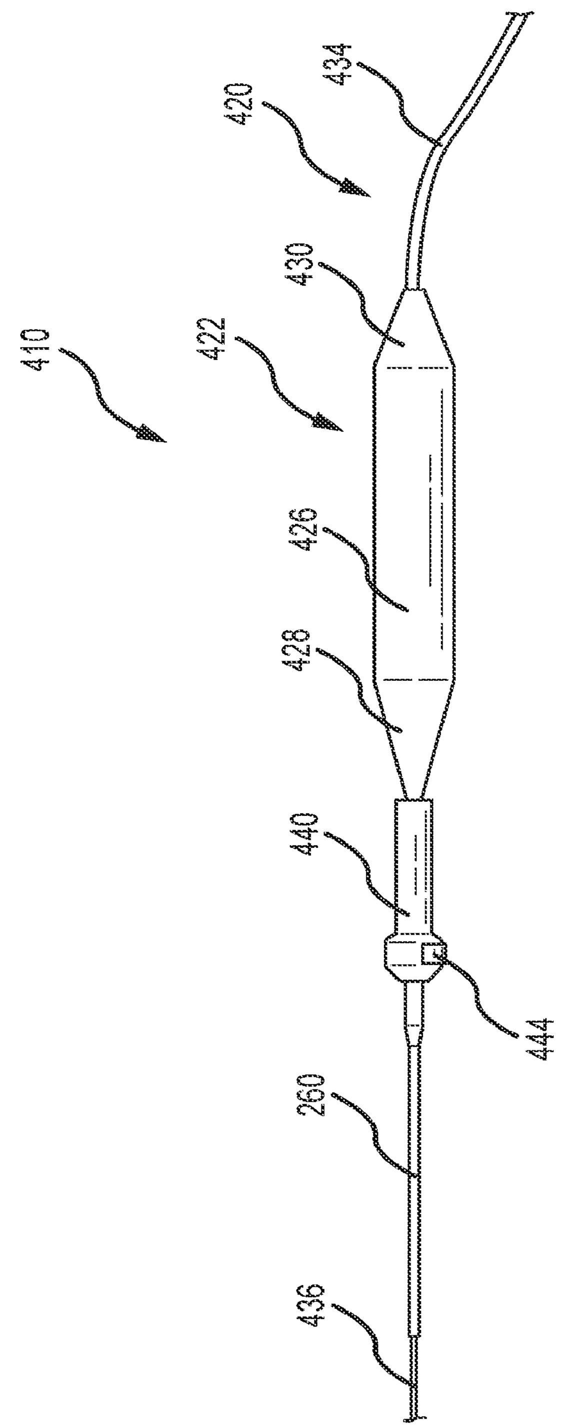
FIG. 9A is a perspective view of an embodiment of a catheter assembly that utilizes both an electrical housing and a separate catheter shaft actuator.
Figure 9B:
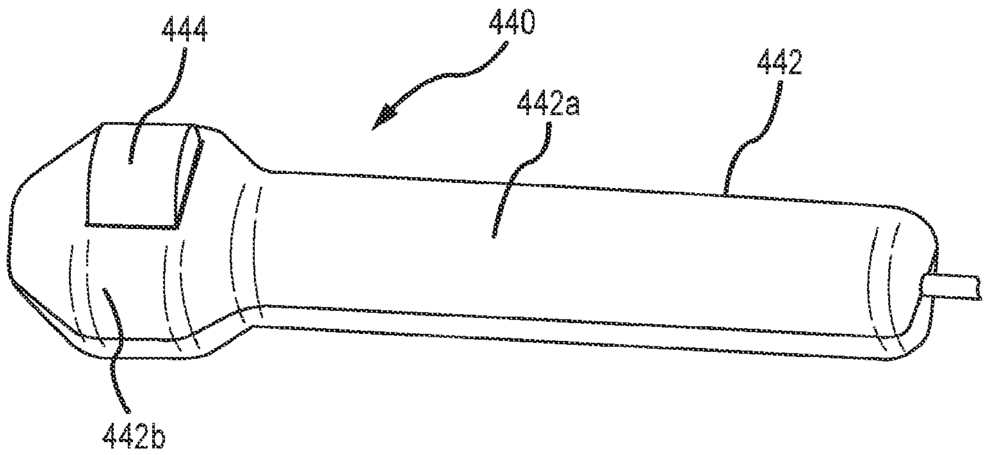
FIG. 9B is a perspective view of the catheter shaft actuator for the catheter assembly of FIG. 9A.
Figure 9C:
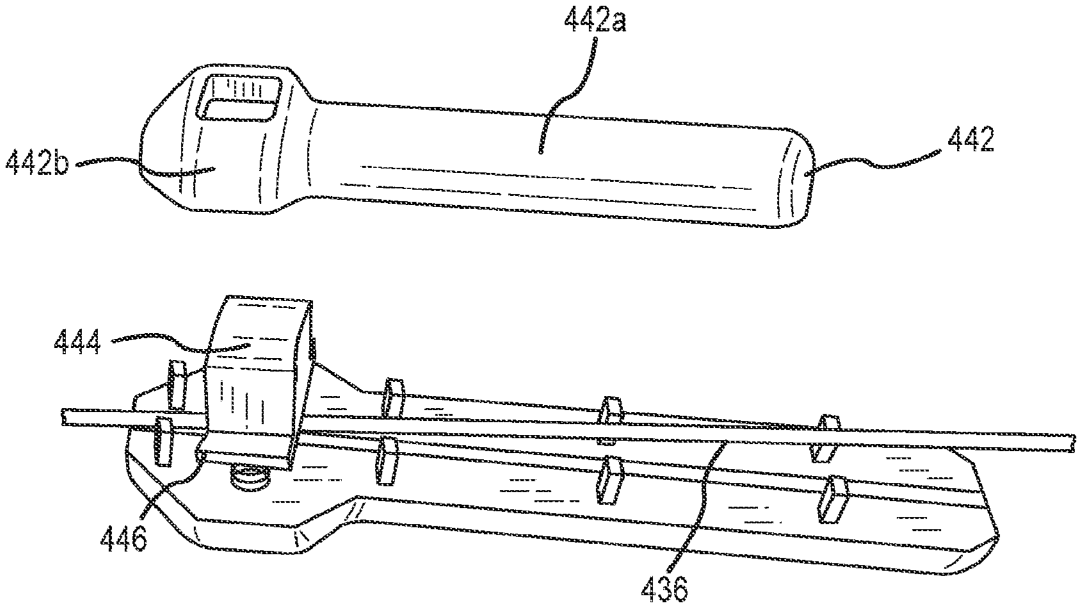
FIG. 9C is an exploded, perspective view of the catheter shaft actuator for the catheter assembly of FIG. 9A.
Figure 9D:
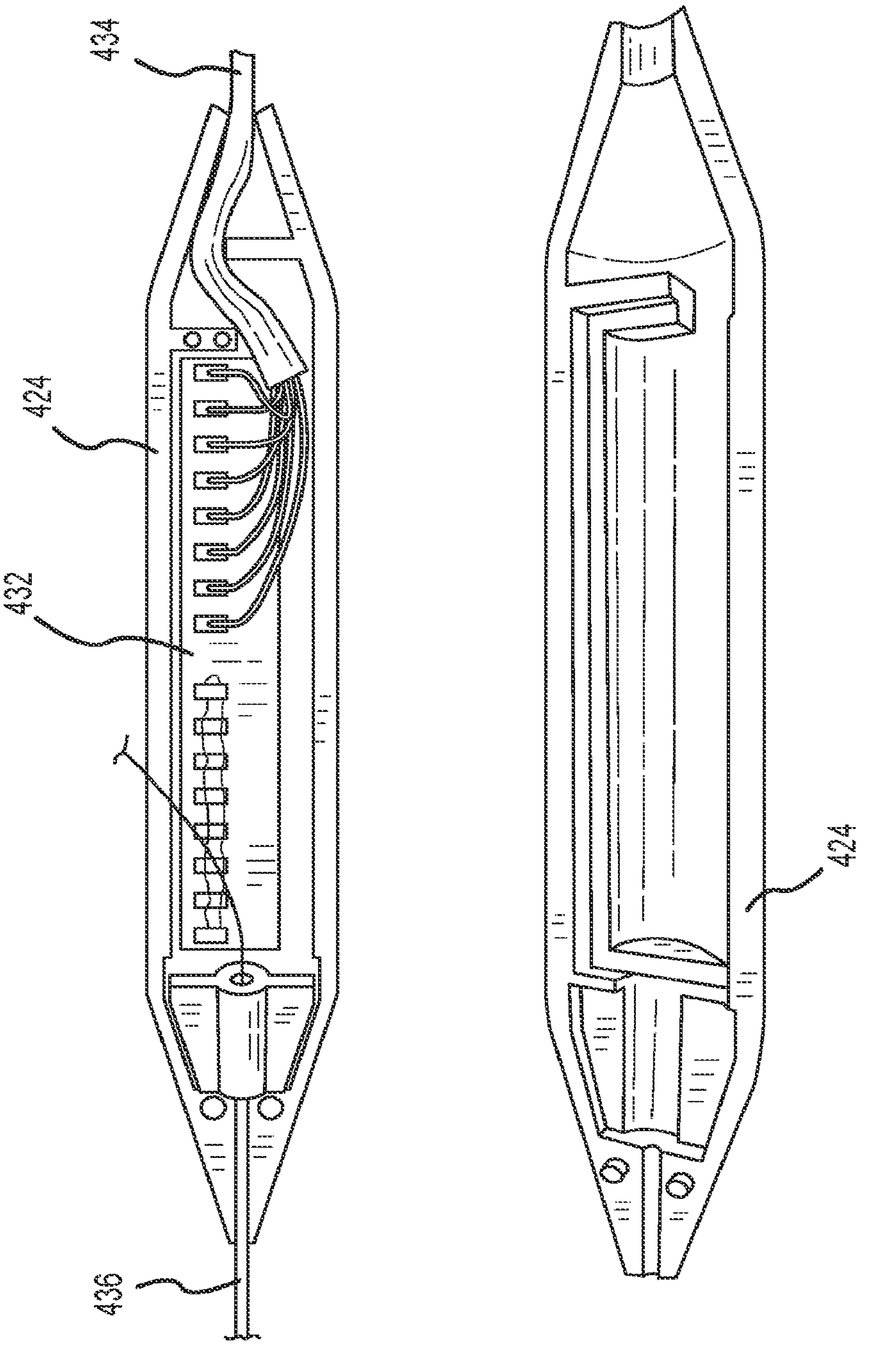
FIG. 9D is an exploded, perspective view of the electrical housing for the catheter assembly of FIG. 9A.

The clamping actuator 390 may be disposed in its released configuration (by movement of the actuator 390, to produce a corresponding movement of the clamp 392) such that the catheter shaft actuator 370 may be advanced distally along the catheter shaft 364, to thereby position the catheter shaft actuator 370 closer to the vasculature access being utilized and where the catheter shaft actuator 370 is now spaced from the catheter handle 362, for instance as shown in FIG. 8B. Although such a configuration may be utilized for a femoral access to the patient's vasculature, it of course may also be utilized for a radial access to the patient's vasculature (or any other access to the patient's vasculature). Generally, the catheter shaft actuator 370 may be moved to any position along the catheter shaft 364, and thereafter the clamping actuator 390 may be disposed in its clamping configuration where the clamp 392 clampingly engages the exterior of the catheter shaft 364. In any case and with the clamping actuator 390 being in its clamped configuration, a user may engage the body 372 to exert a desired force or combination of forces on the catheter shaft 218 in the manner described herein and to yield a desired movement or combination of movements of the catheter shaft 218.

Another embodiment of a catheter assembly is illustrated in FIGS. 9A-9D and is identified by reference numeral 410. There are three primary components/subassemblies of the catheter assembly 410—a catheter 420, a catheter shaft actuator 440, and the above-described straightening tool 260.

The catheter 420 may be of any appropriate type/configuration and may provide any appropriate function or combination of functions when disposed in a patient's vasculature (e.g., diagnostic, therapeutic, neuromodulation, denervation). The catheter 420 includes an electrical housing 422 and a catheter shaft 436 that extends distally from a distal end of the electrical housing 422. The catheter shaft 436 may extend at least into the distal end of the electrical housing 422. A generator cable 434 extends proximally from a proximal end of the electrical housing 422.

The electrical housing 422 may be defined by a pair of housing sections 424 that are appropriately interconnected. A printed circuit board 432 is enclosed within the electrical housing 422. The printed circuit board 432 may include one or more bonding pads to provide an electrical/operative connection between the wires for any electrodes or other electrical components incorporated by the catheter shaft 436 (e.g., electrodes 224) and the generator cable 434. Any appropriate structure for providing an electrical/operative connection between the wires for the electrodes/electrical components of the catheter shaft 436 and the generator cable 434 may be utilized by the electrical housing 422.

In the case of the catheter assembly 410, the electrical housing 422 is not in the form of a traditional catheter handle. Instead the primary function of the electrical housing 422 is to enclose the printed circuit board 432 (or more generally the structure for providing an electrical/operative connection between the wires 226 for the electrodes 224 and the generator cable 434). The electrical housing 422 is subject to a number of characterizations in this regard. One is that the exterior of the housing 422 is not ergonomically shaped. Another is that a maximum outer diameter of the housing 422 (taken perpendicular to its length dimension) is reduced compared to typical catheter handles. In the illustrated embodiment, the housing 422 includes a cylindrical section 426, a distal end section 428, and a proximal end section 430, with the cylindrical section 426 being disposed between the distal end section 428 and the proximal end section 430, and with the distal end section 428 and the proximal end section 430 being spaced from one another along a length dimension of the housing 422. The distal end section 428 converges toward a centerline through the housing 422 (corresponding with the length dimension of the housing 422) proceeding in the distal direction from the cylindrical section 426. Similarly, the proximal end section 430 converges toward the centerline through the housing 422 proceeding in the proximal direction from the cylindrical section 426.

The catheter shaft actuator 440 is positioned on the distal side of the housing 422, includes a housing 442, an actuator 444, and a clamp 446, and provides the primary structure for moving the catheter shaft 436 in the case of the catheter assembly 410. The housing 442 includes a proximal housing section 442*a* and a distal housing section 442*b*. The distal housing section 442*b* incorporates the actuator 444 and the clamp 446. A user may grasp the proximal housing section 442*a* to move the catheter shaft 436 in the desired manner. As such, the proximal housing section 442*a* may also be referred to as a "catheter shaft actuator 442*a*."

The actuator 444 is disposed on an exterior of the catheter shaft actuator 440 and is movable between first and second positions to dispose the clamp 446 in a released configuration and a clamping configuration, respectively. As such, the actuator 444 may also be referred to as a "clamping actuator 444." Disposing the clamping actuator 444 in its released configuration (by movement of the actuator 444, to produce a corresponding movement of the clamp 446) allows the catheter shaft actuator 440 to be advanced along and relative to the catheter shaft 436 to a desired location (e.g., in proximity to the access to the patient's vasculature, whether using a femoral access, a radial access, or any other vasculature access). Disposing the clamping actuator 444 in its clamping configuration (by movement of the clamping actuator 444, to produce a corresponding movement of the clamp 446) allows the clamping actuator 444 (more specifically the clamp 446) to engage an exterior of the catheter shaft 436 such that rotation of the catheter shaft actuator 440 (e.g., about a centerline coinciding with a length dimension of the catheter shaft actuator 440, which coincides with the length of the catheter shaft 436 extending through the catheter shaft actuator) will correspondingly rotate the catheter shaft 436 about its length dimension, and such that advancement of the catheter shaft actuator 440 (e.g., by engagement of and pushing or pulling on the catheter shaft actuator 440) will advance the catheter shaft 436 along the patient's vasculature in the corresponding direction. Generally, the catheter shaft actuator 440 may be moved to any position along the catheter shaft 436 that is desired by the user, and thereafter with the clamping actuator 444 being in its clamped configuration, a user may engage the catheter shaft actuator 440 to exert a desired force or combination of forces on the catheter shaft 436 in the manner described herein and to yield a desired movement or combination of movements of the catheter shaft 436.

Figure 10A:
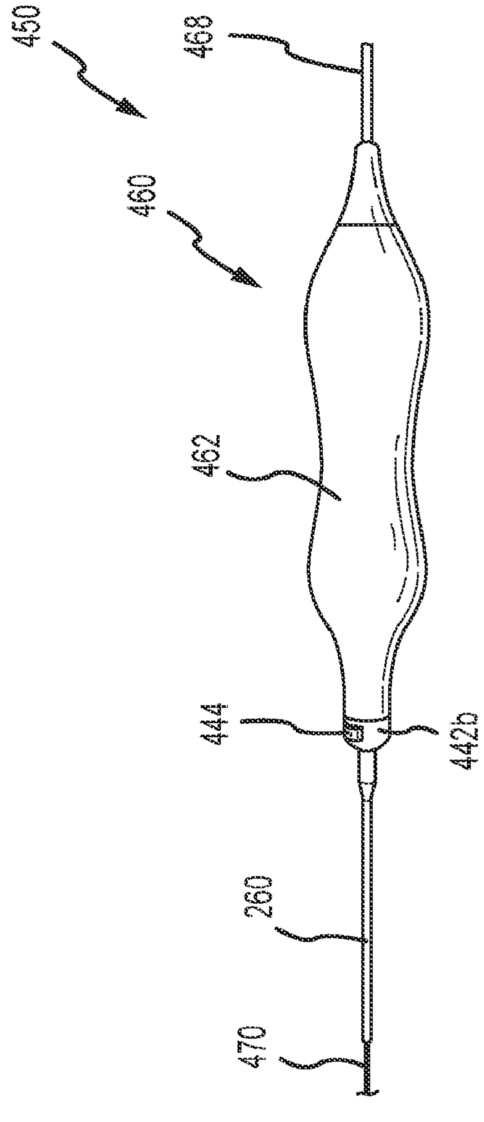
FIG. 10A is a perspective view of another embodiment of a catheter assembly that utilizes both a catheter handle and a separate catheter shaft actuator, and with the catheter shaft actuator in a first position relative to the catheter handle.
Figure 10B:
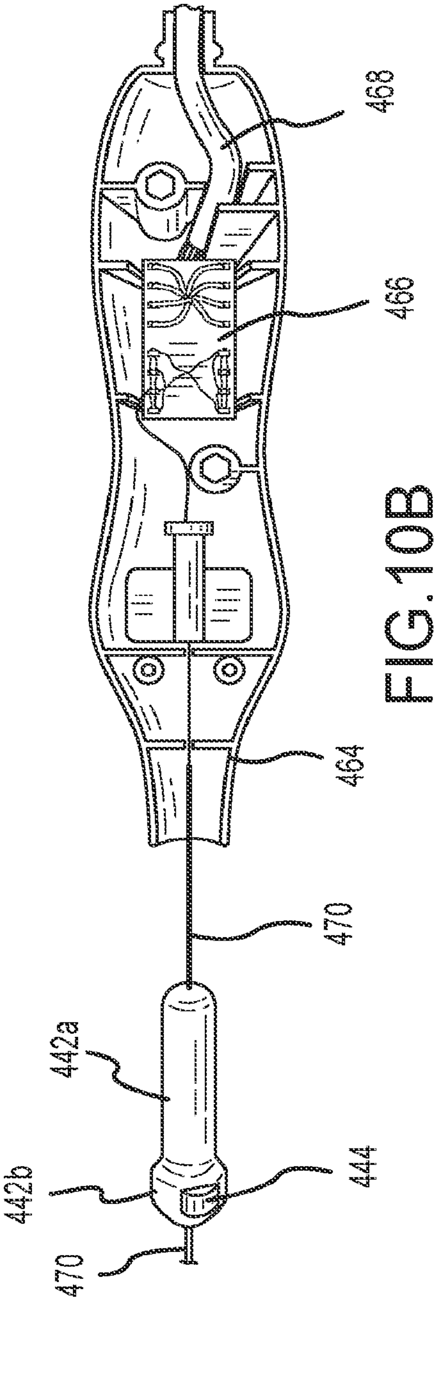
FIG. 10B is a cutaway view of the catheter assembly of FIG. 10A, with the catheter shaft actuator being in a second position relative to the catheter handle.

Another embodiment of a catheter assembly is illustrated in FIGS. 10A-10B and is identified by reference numeral 450. There are three primary components/subassemblies of the catheter assembly 450—a catheter 460, the above-described catheter shaft actuator 440, and the above-described straightening tool 260.

The catheter 460 may be of any appropriate type/configuration and may provide any appropriate function or combination of functions when disposed in a patient's vasculature (e.g., diagnostic, therapeutic, neuromodulation, denervation). The catheter 460 includes a catheter handle 462 and a catheter shaft 470 that extends distally from a distal end of the catheter handle 462. The catheter shaft 470 may extend at least into the distal end of the catheter handle 462, and may be of any appropriate configuration (e.g., in accord with the above-discussed catheter shaft 218). The catheter shaft 470 may be appropriately anchored/fixed relative to the catheter handle 462 to allow the catheter handle 462 to be used to torque the catheter shaft 470 (e.g., in the FIG. 10A configuration), to be used to advance the catheter handle 462 (e.g. by pushing or pulling on the catheter handle 462 to advance the catheter shaft 470 relative to the patient's vasculature in a corresponding direction), or both. A generator cable 468 extends proximally from a proximal end of the catheter handle 462.

The catheter handle 462 may be defined by a pair of handle sections 464 that are appropriately interconnected (only one handle section 464 being shown in FIG. 10B). A printed circuit board 466 is enclosed within the catheter handle 462. The printed circuit board 466 may include one or more bonding pads to provide an electrical/operative connection between the wires for any electrodes or other electrical components incorporated by the catheter shaft 470 (e.g., electrodes 224) and the generator cable 468. Any appropriate structure for providing an electrical/operative connection between the wires for the electrodes (or other electrical components incorporated by the catheter shaft 470) and the generator cable 468 may be utilized by the catheter handle 462.

The distal housing section 442*b* of the catheter shaft actuator 440 is disposed distally of the catheter handle 462 and the proximal housing section 442*a* is disposed within the catheter handle 462 in the FIG. 10A configuration (e.g., for radial access, or any other appropriate vasculature access). Again, the clamping actuator 444 is disposed on an exterior of the catheter shaft actuator 440 (specifically the distal housing section 442*b*) and is movable between first and second positions to again dispose the clamp 446 in a released configuration and a clamping configuration, respectively. Disposing the clamping actuator 444 in its released configuration (by movement of the actuator 444, to produce a corresponding movement of the clamp 446) allows the catheter shaft actuator 440 to be advanced along and relative to the catheter shaft 470 to a desired location (e.g., in proximity to the access to the patient's vasculature, whether using a femoral access, a radial access, or any other vasculature access). Disposing the clamping actuator 444 in its clamping configuration (by movement of the actuator 444, to produce a corresponding movement of the clamp 446) allows the clamping actuator 444 (more specifically the clamp 446) to engage an exterior of the catheter shaft 470 such that rotation of the catheter shaft actuator 440 (e.g., about a centerline coinciding with a length dimension of the catheter shaft actuator 440, which coincides with the length of the catheter shaft 436 extending through the catheter shaft actuator 440) will correspondingly rotate the catheter shaft 436 about its length dimension, and such that advancement of the catheter shaft actuator 440 (e.g., by engagement of and pushing or pulling on the catheter shaft actuator 440) will advance the catheter shaft 436 along the patient's vasculature in the corresponding direction. Generally, the catheter shaft actuator 440 may be moved to any position along the catheter shaft 470 that is desired by the user, and thereafter with the clamping actuator 444 being in its clamped configuration, a user may engage the catheter shaft actuator 440 to exert a desired force or combination of forces on the catheter shaft 436 in the manner described herein and to yield a desired movement or combination of movements of the catheter shaft 470.

Features may be incorporated to detachably connect the catheter handle 462 and the catheter shaft actuator 470, for instance when in the FIG. 10A configuration, although such is not required. In any case and in the FIG. 10A configuration, the catheter shaft handle 462 may be used to torque the catheter shaft 470 (e.g., by a user engaging the catheter handle 462 and rotating the same about the length dimension of the catheter shaft 470). For instance, the configuration shown in FIG. 10A could be for a radial access to the patient's vasculature. Disposing the clamping actuator 444 in its clamping configuration (by movement of the actuator 444, to produce a corresponding movement of the clamp 446), again allows the catheter shaft actuator 440 (more specifically the clamp 446) to engage an exterior of the catheter shaft 470. This may be used to maintain the catheter shaft actuator 440 in a fixed position relative to the catheter handle 462 for the FIG. 10A configuration. Having the clamping actuator 444 in its clamping configuration when the catheter shaft actuator 440 is disposed in the FIG. 10A configuration (even when the user is engaging the catheter handle 462 to exert a force on the catheter shaft 470), however, may also further facilitate the desired movement of the catheter shaft 470, as the catheter handle 462 and the clamp 444 would be engaging the catheter shaft 470 at spaced locations and each of these engagements alone should accommodate the desired movement of the catheter shaft 470 (whether via manipulation of the catheter shaft actuator 440 (specifically distal housing section 442*b*) or the catheter handle 462).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

Any feature of any other various aspects addressed in this disclosure that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular. Moreover, any failure to use phrases such as "at least one" also does not limit the corresponding feature to the singular. Use of the phrase "at least substantially," "at least generally," or the like in relation to a particular feature encompasses the corresponding characteristic and insubstantial variations thereof (e.g., indicating that a surface is at least substantially or at least generally flat encompasses the surface actually being flat and insubstantial variations thereof). Finally, a reference of a feature in conjunction with the phrase "in one embodiment" does not limit the use of the feature to a single embodiment.

The invention claimed is:

1. A multi-function catheter shaft tool, comprising:
- a tool distal end;
- a tool proximal end;
- a lumen that extends from the tool distal end to the tool proximal end, wherein the lumen is sized to accommodate a catheter shaft;
- a catheter shaft straightener extending to at least the tool distal end, the catheter shaft straightener comprising:
  - a liner, wherein the lumen extends through the liner; and an outer housing disposed about the liner along at least part of a length of the liner, wherein the liner comprises a first hardness and the outer housing comprises a second hardness that is greater than the first hardness, and wherein the outer housing is more rigid than the liner, and wherein the liner extends distally beyond a distal end of the outer housing, and wherein the liner extends to the tool distal end;

a catheter shaft actuator, wherein the catheter shaft straightener extends proximally from the tool distal end and at least to a distal end of the catheter shaft actuator, wherein the catheter shaft straightener and the catheter shaft actuator are configured to be collectively rotatable; and a catheter shaft clamp disposable in each of a clamping configuration and a released configuration relative to the lumen.

2. The multi-function catheter shaft tool of claim 1, wherein the catheter shaft straightener comprises a flared distal end section.

3. The multi-function catheter shaft tool of claim 1, further comprising a clamping actuator operatively interconnected with the catheter shaft clamp.

4. The multi-function catheter shaft tool of claim 1, wherein the catheter shaft clamp comprises a clamping section that is interconnected with a proximal end of the liner.

5. The multi-function catheter shaft tool of claim 4, wherein the clamping section is of a hardness that is greater than a hardness of the liner.

6. The multi-function catheter shaft tool of claim 4, wherein the clamping section comprises at least two inwardly deflectable sections, and wherein an interior of the catheter shaft actuator is configured to engage both the outer housing and the at least two inwardly deflectable sections of the clamping section.

7. The multi-function catheter shaft tool of claim 6, wherein advancement of the catheter shaft actuator toward the tool distal end and relative to the catheter shaft straightener moves the at least two inwardly deflectable sections of the clamping section in a radially inward direction.

8. The multi-function catheter shaft tool of claim 6, wherein the catheter shaft actuator is detachably engageable with the outer housing, wherein a proximal end section of the outer housing comprises external threads and the catheter shaft actuator comprises internal threads that are configured to threadably engage with the external threads of the proximal end section of the outer housing, and wherein threading the catheter shaft actuator toward the tool distal end exerts a radially inwardly directed force on the at least two inwardly deflectable sections of the clamping section.

9. The multi-function catheter shaft tool of claim 1, wherein the catheter shaft actuator is operable to at least one of torque a catheter shaft or advance the catheter shaft when the catheter shaft extends through the lumen and when the catheter shaft clamp is disposed in the clamping configuration.

10. A catheter system comprising:

the multi-function catheter shaft tool of claim 1; and a catheter, wherein the catheter comprises a catheter shaft that in turn comprises a non-linear section, wherein the non-linear section of the catheter shaft is configured to be forced into a straighter profile when disposed within the catheter shaft straightener compared to when the non-linear section of the catheter shaft is disposed distally beyond the catheter shaft straightener.

11. The catheter system of claim 10, wherein the catheter comprises a catheter handle, and wherein the catheter shaft actuator is disposed distally of the catheter handle when the catheter shaft is positioned in the lumen.

12. The catheter system of claim 10, wherein the non-linear section of the catheter shaft defines a distal section of the catheter shaft.

13. The multi-function catheter shaft tool of claim 1, wherein an outer diameter of the catheter shaft actuator is greater than a maximum outer diameter of the catheter shaft straightener.

14. A method of manipulating a catheter, the catheter comprising a catheter shaft that in turn comprises a non-linear section, the method comprising:

directing the non-linear section of the catheter shaft into a distal end of a multi-function catheter shaft tool to dispose the non-linear section within a catheter shaft straightener of the multi-function catheter shaft tool, wherein directing the non-linear section into the catheter shaft straightener forces the non-linear section toward a straighter profile, the multi-function catheter shaft tool comprising a lumen that extends from a tool distal end to a tool proximal end of the multi-function catheter shaft tool, wherein the catheter shaft straightener comprises:

a liner, wherein the lumen extends through the liner; and an outer housing disposed about the liner along at least part of a length of the liner, wherein the liner comprises a first hardness and the outer housing comprises a second hardness that is greater than the first hardness, and wherein the outer housing is more rigid than the liner, and wherein the liner extends distally beyond a distal end of the outer housing, and wherein the liner extends to the tool distal end;

after directing the non-linear section into the catheter shaft straightener, executing a first moving step comprising moving the multi-function catheter shaft tool in a proximal direction along and relative to the catheter shaft, and with the multi-function catheter shaft tool being in a released configuration;

after moving the multi-function catheter shaft tool in the proximal direction, disposing the multi-function catheter shaft tool in a clamping configuration where the multi-function catheter shaft tool engages an exterior of the catheter shaft; and moving the catheter shaft with the multi-function catheter shaft tool being in the clamping configuration and by exerting an external force on the multi-function catheter shaft tool.

15. The method of claim 14, wherein the non-linear section of the catheter shaft is in an expanded configuration without any force being exerted on the non-linear section, and wherein directing the non-linear section into the catheter shaft straightener reduces a profile step of the non-linear section.

16. The method of claim 14, wherein the multi-function catheter shaft tool is mounted on the catheter shaft with the multi-function catheter shaft tool being located proximally of the non-linear section of the catheter shaft, and wherein directing the non-linear section into the distal end of the multi-function catheter shaft tool comprises distally advancing the multi-function catheter shaft tool along the catheter shaft in a direction of the non-linear section of the catheter shaft.

17. The method of claim 14, wherein moving the multi-function catheter shaft tool in the proximal direction comprises torquing the catheter shaft, and moving an entirety of the multi-function catheter shaft tool, including the catheter shaft straightener, in a rotational direction.

18. The method of claim 14, further comprising:

loading a guidewire into a distal end of the catheter shaft after directing the non-linear section into the catheter shaft straightener.

* * * * *